United States Patent [19]

Mitsuhashi et al.

[11] 4,452,786
[45] Jun. 5, 1984

[54] CONDURANGO GLYCOSIDE COMPOUNDS, PROCESSES FOR THEIR PREPARATION, ANTITUMOR AGENTS COMPRISING THEM AND COMPOSITIONS

[75] Inventors: Hiroshi Mitsuhashi, Hokkaido; Den-ichi Mizuno, Kanagawa; Koji Hayashi, Hokkaido; Shigeru Abe, Kanagawa; Muneaki Takase; Toshiharu Narita, both of Tokyo, all of Japan

[73] Assignee: Zenyaku Kogyo Kabushiki Kaisha, Tokyo, Japan

[21] Appl. No.: 320,974

[22] PCT Filed: Mar. 5, 1981

[86] PCT No.: PCT/JP81/00045
§ 371 Date: Nov. 2, 1981
§ 102(e) Date: Nov. 2, 1981

[87] PCT Pub. No.: WO81/02577
PCT Pub. Date: Sep. 17, 1981

[30] Foreign Application Priority Data

Mar. 5, 1980 [JP] Japan .................. 55-27697
May 31, 1980 [JP] Japan .................. 55-73594
Jul. 9, 1980 [JP] Japan .................. 55-93544
Sep. 9, 1980 [JP] Japan .................. 55-125175

[51] Int. Cl.³ .................. A61K 31/71; A61K 31/705; C07H 15/24; C07J 17/00
[52] U.S. Cl. .................. 424/182; 424/180; 536/5; 536/18.1
[58] Field of Search .................. 424/180, 182; 536/4.1, 536/5, 6.1, 18.1

[56] References Cited

U.S. PATENT DOCUMENTS

| | | | |
|---|---|---|---|
| 2,557,916 | 6/1951 | Rosen et al. | 536/6.3 |
| 2,780,620 | 2/1957 | Krider et al. | 536/6.3 |
| 3,907,775 | 9/1975 | Losel et al. | 536/6.1 |
| 3,960,839 | 6/1976 | Guerrero | 536/6.3 |
| 4,000,125 | 12/1976 | Casagrande et al. | 536/5 |
| 4,084,010 | 4/1978 | Takemoto et al. | 536/5 |
| 4,157,894 | 6/1979 | Bombardelli | 536/5 |

*Primary Examiner*—Johnnie R. Brown
*Attorney, Agent, or Firm*—Browdy & Neimark

[57] ABSTRACT

Novel condurango glycoside compounds, antitumor agents comprising them and processes for their preparation, compositions containing them and methods of treating tumor with them are disclosed herein in which the novel condurango glycoside compounds are represented by the following formula (I):

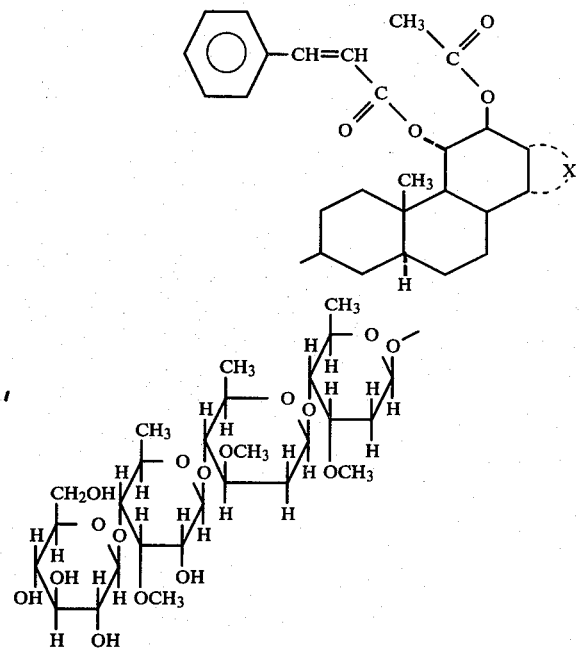

where X together with the 13 and 14 position carbon atoms is a group selected from the group consisting of

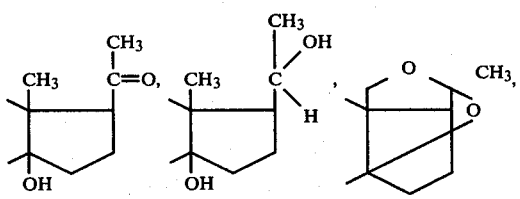 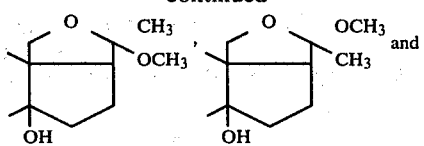 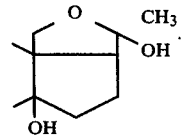
8 Claims, 19 Drawing Figures

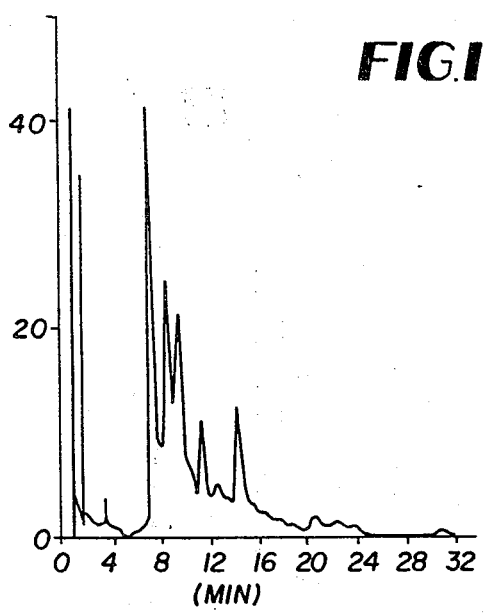
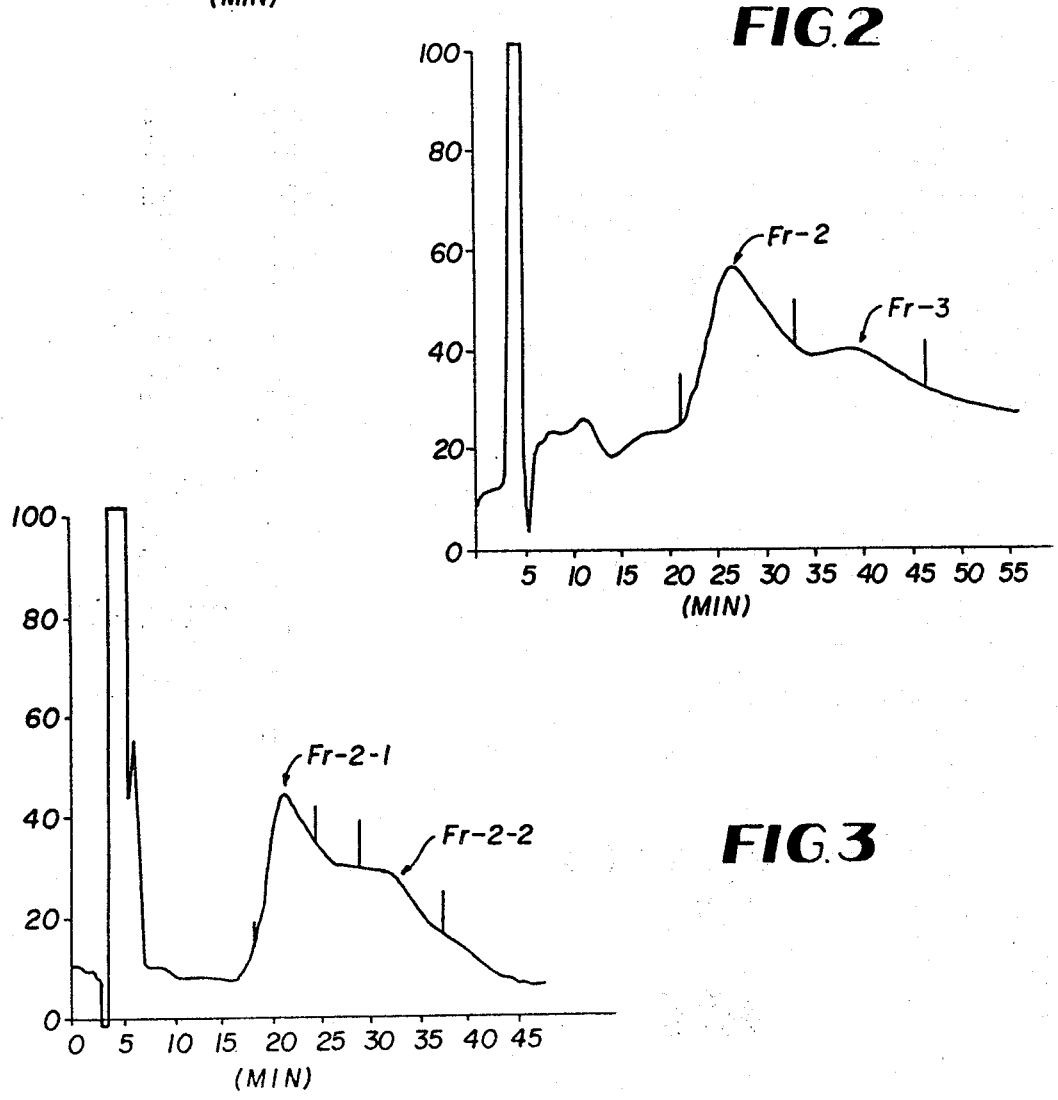

FIG.4
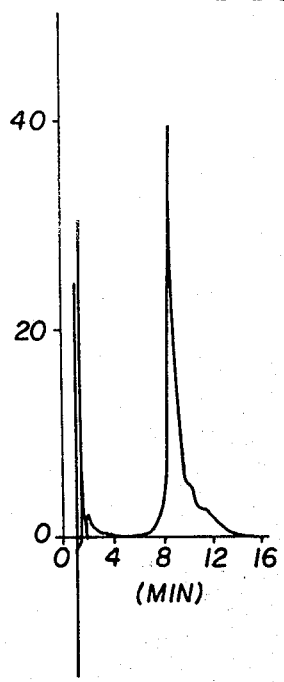
FIG.5
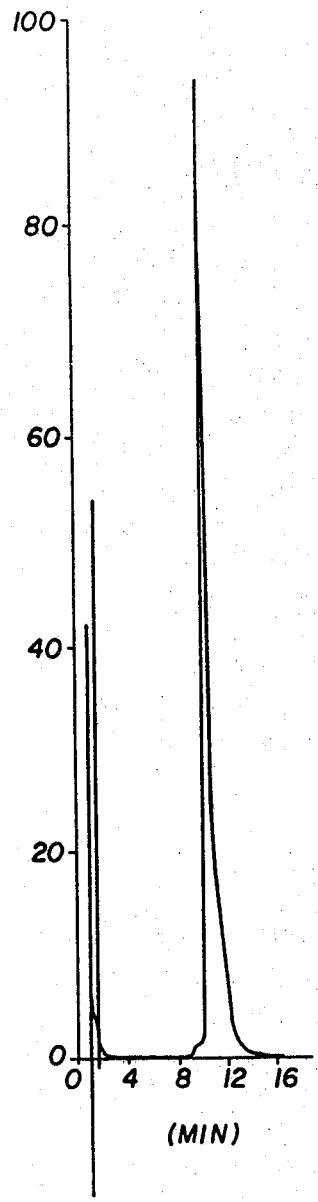
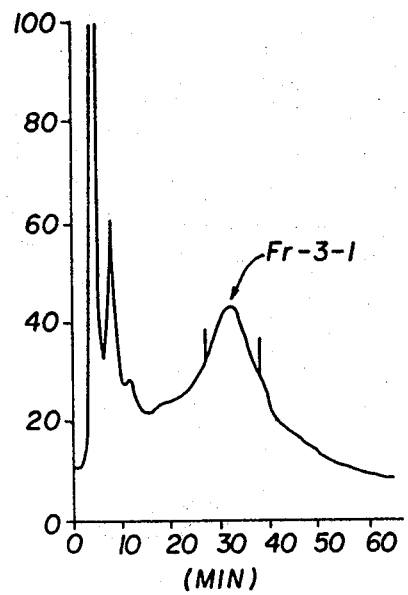
FIG.6

CONDURANGO GLYCOSIDE COMPOUNDS, PROCESSES FOR THEIR PREPARATION, ANTITUMOR AGENTS COMPRISING THEM AND COMPOSITIONS

TECHNICAL FIELD

The present invention relates to novel compounds obtained from *Marsdenia cundurango* Reichenbach fil. and represented by the general formula (I) given below, processes for their preparation, antitumor agents comprising them and compositions containing them.

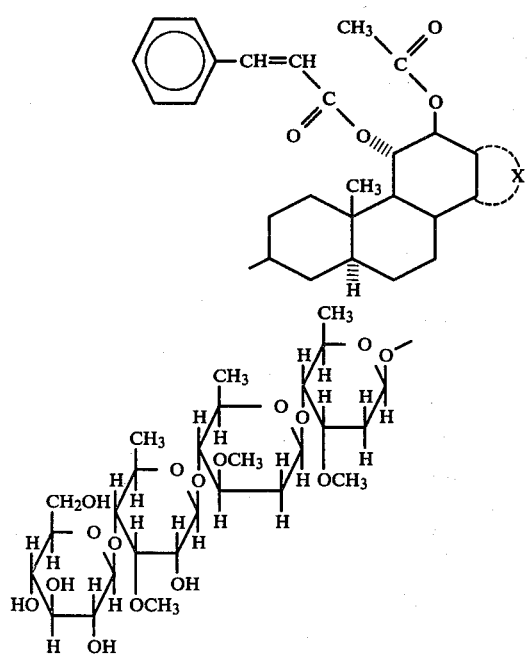

where X together with the 13 and 14 position carbon atoms is a group selected from the group consisting of

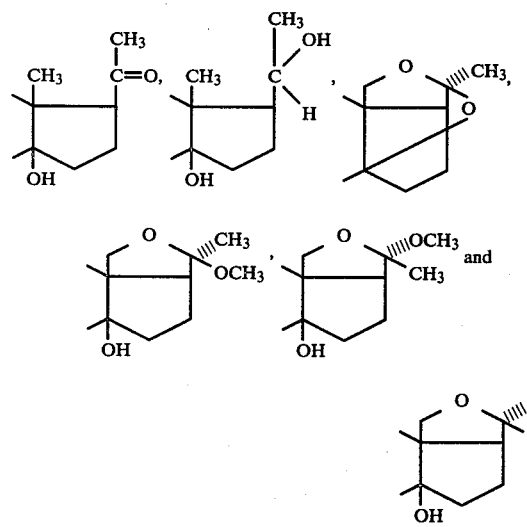

The compounds of the above general formula are named condurango glycoside $A_o$, condurango glycoside $C_o$, condurango glycoside $B_o$, 20-O-methyl-condurango glycoside $D_o$, 20-iso-O-methyl-condurango glycoside $D_o$ and condurango glycoside $D_o$ when X is

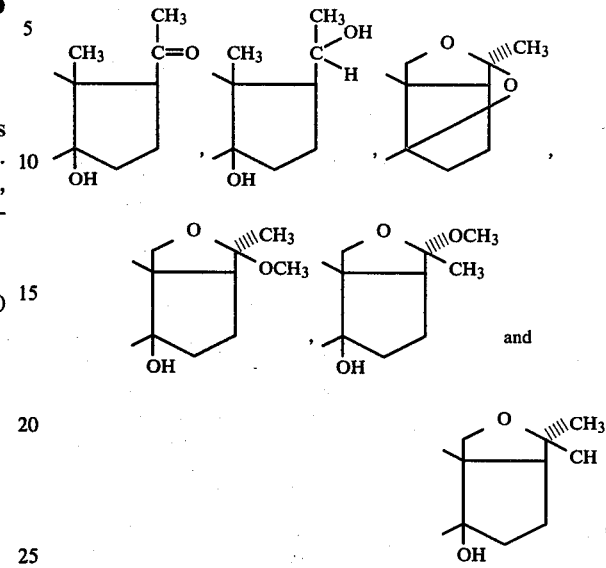

respectively.

BACKGROUND ART

*Marsdenia cundurango* Reichenbach fil. belonging to the family Asclepiadaceae is a shrub of somewhat winding type growing naturally on and between mountains in the northwest of South America. Its bark is employed as an aromatic but bitter stomachic at the time of digestive disorder and/or anorexia, usually in the form of fluidextract (Commentary for the ninth Japanese Pharmacopeia)

The components of the bark of *Marsdenia cundurango* Reichenbach fil. include condurangogenin-A, condurangogenin-C and many other pregnane type compounds and their esters and glycosides, and the extraction, separation, structures and so on of them have been reported in, for example, the following documents. R. Tschesche et al., Tetrahedron, 21, p. 1777 (1965); 21, p. 1797 (1965); 23, p. 1461 (1967); and 24, p. 4359 (1968). M. Pailar et al., Monatshefte für Chemie, 106, p. 37 (1975). Hiroshi Mitsuhashi et al., Chem. Pharm. Bull., 16, p. 2522 (1968). But details are still unclear in many respects.

As a result of study, the inventors of the present inventinon have found novel compounds represented by the above general formula (I) which have antitumor activity. The present invention has been completed on the basis of this finding.

DISCLOSURE OF THE INVENTION

In carrying out the present invention, the bark of *Marsdenia cundurango* Reichenbach fil. is preferred. This bark may be one commercially available, but is preferably one well dried and finely divided after its collection.

In view of the nature of the preparation of extracts, the order of the use of solvents is not critical in carrying out the present invention, and it may be changed according to convenience. A preferred embodiment of the process of the present invention is as follows:

First Operation

*Marsdenia cundurango* Reichenbach fil. if finely divided and extracted with an organic solvent, and the extract is concentrated to dryness under reduced pressure. As the organic solvent, methanol, ethanol, isopropanol or any other lower alcohol may be employed, but methanol is preferred.

Here, prior to the extraction, *Marsdenia cundurango* Reichenbach fil. may be defatted with an aliphatic hydrocarbon such as pentane, hexane, heptane, ligroine or petroleum ether. This pre-treatment is desired to be effected using hexane in an amount 4–7 times (v/w) that of *Marsdenia cundurango* Reichenbach fil.

In an embodiment of this extraction operation, first the extraction is effected by allowing the starting material-solvent mixture to stand at room temperature for from several hours to 12 hours or more. Then, the mixture is filtered to yield a filtrate. The residue is subjected to the same extraction-filtration repeatedly, and all the filtrates are combined and concentrated to dryness under reduced pressure to yield an extract.

The extraction is usually effected at normal temperatures, but may be effected while heating in order to shorten the extraction time. This extraction with heating is preferably carried out on a water bath at a water bath temperature of 35°–55° C. for 4–6 hours using a reflux condenser. It may be effected according to the percolation method.

The amount of the solvent used is 2–5 times (v/w) that of *Marsdenia cundurango* Reichenbach fil. The extraction residue is preferably subjected to extraction under the same conditions three or more times using the solvent in an amount 0.4–0.8 times (v/v) that of the solvent first used.

The separation may be conducted by paper filtration, centrifugation or the like. Better results are given by conducting the separation by suction filtration using commercially available filtration additives, for example, Radiolite (Showa Chemical Industry Co., Ltd. in Japan), Celite (Wako Junyaku Industry Co., Ltd. in Japan), Fibra Cel (Johns Manville Co., Ltd. in U.S.A.), etc.

The reduction in pressure is conducted in a usual manner, for example, using an aspirator, vacuum pump or the like.

As the extraction vessel, one with a glass-lined or enameled inner surface or one made of stainless steel is employed.

Second operation

To the extract obtained by the first operation, there is added a chlorinated hydrocarbon other than carbon tetrachloride such as chloroform or dichloromethane followed by vigorous shaking to remove the insoluble portion. The insoluble portion is subjected to the same operation repeatedly. All the remaining solutions are combined and concentrated to dryness under reduced pressure directly or after suction filtration. The amount of the solvent used is 2–6 times (v/w) that of the extract obtained by the first operation. The respective insoluble portions are preferably subjected to the same operation four or five times, but using the solvent in an amount of 0.2–0.4 times (v/v) that of the solvent first used.

The suction filtration may be carried out in the same manner as in the first operation.

Third operation

The extract obtained by the second operation is dissolved in a chlorinated hydrocarbon other than carbon tetrachloride such as chloroform or dichloromethane in the minimum amount necessary to dissolve the extract completely. To the resulting solution, there is added an aliphatic hydrocarbon such as pentane, n-hexane or heptane in an amount two to four times (v/v) that of the former followed by stirring and allowing to stand for from several hours to 12 hours or more to collect the insoluble portion. Alternatively, carbon tetrachloride or an aromatic hydrocarbon such as toluene or benzene may be added to the extract directly in an amount the same as or up to three times (v/w) that of the latter and then be worked up as in the above to collect the insoluble portion.

The insoluble portion is subjected to the same operation repeatedly. This operation is preferably conducted two or three times, each time using the solvent in an amount 0.4–0.6 times (v/v) that of the solvent first used. The thus obtained insoluble portion is well dried at a temperature of 50° C. or less under reduced pressure and then crushed to yield a brown powder-like extract (hereunder referred to as Extract A).

The collection of the insoluble portion may be made by decantation, suction filtration or centrifugation.

In order to lower the total cost of the process of the present invention and to make the operation easier to follow, finely divided *Marsdenia cundurango* Reichanbach fil. may first be extracted with an aliphatic ketone such as acetone or methyl ethyl ketone, a lower aliphatic ester such as methyl acetate, ethyl acetate or butyl acetate, an ether such as diethyl ether, tetrahydrofuran or dioxane or hot water or be treated with heat (110°–130° C. for 30 min.) directly followed by the extraction with water or an aqueous lower alcohol, and then the extract may be subjected to the above mentioned three operations. Here, the extraction may be carried out in the same manner as in the above described first operation.

The thus obtained Extract A is a mixture showing six characteristic peaks in the chart depicted in FIG. 1 (hereunder, the number stands for that of the accompanying drawings) when subjected to normal phase analytical chromatography (HPLC), and has antitumor activity.

Fourth operation

Extract A from the third operation is dissolved in chloroform in the minimum amount necessary for its complete dissolution, and to the resulting solution there is added n-hexane in such an amount that the solution does not become turbid. The obtained sample solution is subjected to normal phase HPLC [eluant: n-hexane/chloroform/methanol mixture (volumetric ratio=6:3:1)]. Here, throughout the specification and the claims, HPLC means HPLC for collection unless otherwise indicated. While observing elution peaks with a detector, two fractions, chosen on the basis of the peaks corresponding to Fr-2 and Fr-3 fractions depicted in the chart (FIG. 2) obtained beforehand by preliminary tests, are collected, respectively (in the subsequent HPLC operations, the collection of the object fraction is effected in the same way). Then each fraction is concentrated to dryness to yield extracts.

Alternatively, Extract A obtained by the third operation may be subjected to the open column method eluting successively with chloroform and a chloroform/methanol mixture (volumetric ratio=97:3–95:5) to remove the lesser polar portion, and then eluting with a chloroform/methanol mixture (volumetric ratio=93:7) to yield two fractions corresponding to Fr-2 and Fr-3 fractions mentioned above followed by concentration to dryness. Here, usually the first half of the eluate corresponds to Fr-2 fraction, and the latter half, to Fr-3 fraction, but the volumetric ratio of the two fractions is desired to be 60:40.

Next, the dry extract corresponding to Fr-2 fraction is, as mentioned above, subjected to normal phase HPLC [eluant: n-hexane/chloroform/methanol mixture (volumetric ratio=6:1:1)]. Fractions chosen on the basis of the peaks corresponding to Fr-2-1 and Fr-2-2 fractions (FIG. 3) are collected, respectively, and each is concentrated to dryness to yield white powder-like extracts (hereunder referred to as Extract B-1 and Extract B-2).

The extract corresponding to Fr-3 fraction is subjected to reversed phase HPLC (eluant: 65–75% (v/v) aqueous methanol solution). Fractions chosen on the basis of the peak corresponding to Fr-3-1 fraction (FIG. 6) are collected and concentrated to dryness to yield a white powder-like extract (hereunder referred to as Extract B-3).

Each of Extracts B-1, B-2 and B-3 has antitumor activity.

Fifth operation

This operation is directed to provide the novel compounds of the present invention by subjecting the respective extracts from the fourth operation (Extracts B-1, B-2 and B-3) to fractionation and purification.

Here, in carrying out the following processes for preparation (1)–(4), silica gel and an n-hexane/chloroform/methanol mixture (volumetric ratio=7:2:1) are preferably used as the filler and the eluant for normal phase HPLC, respectively. When reversed phase HPLC is conducted, the filler of the fixed phase is desired to be silica gel with $C_8$ or $C_{18}$ bonded thereto while the eluant is preferably an aqueous mixed solvent, for example, a 40–50% (v/v) aqueous acetonitrile solution, a 75–80% (v/v) aqueous methanol solution or the like. If necessary, the separation and thus the operation may be made easier by the addition of 0.01–0.05% (v/v) of an amine such as diethyl amine or pyridine.

(1) Process for preparing condurango glycoside $B_o$ and 20-O-methyl-condurango glycoside $D_o$ Extract B-1 is subjected to reversed phase HPLC. By referring to the chart depicted in FIG. 8, two fractions corresponding to Fr-4 fraction (fraction of condurango glycoside $B_o$) and Fr-5 fraction (fraction of 20-O-methyl-condurango glycoside $D_o$) are collected separately. The obtained two fractions are subjected to reversed phase HPLC under the same conditions as the above, and two fractions corresponding to Fr-4-1 fraction (FIG. 9) and Fr-5-1 fraction (FIG. 11) are collected separately.

Last, the respective fractions are purified by normal phase HPLC, and the fractions corresponding to the one peak shown in the chart of FIG. 10 or 12 are collected and concentrated to dryness to yield subject compounds as white powder-like materials.

(2) Process for preparing condurango glycoside $A_o$

Extract B-2 is subjected to normal phase HPLC. Fr-2-2-1 fraction corresponding to the one peak shown in the chart of FIG. 13 is collected and then subjected to reversed phase HPLC. A fraction corresponding to the one peak shown in the chart of FIG. 14 is collected and concentrated to dryness to yield subject compound as white powder-like material.

(3) Process for preparing condurango glycoside $C_o$

Extract B-3 is subjected to reversed phase HPLC. A fraction corresponding to the one peak shown in the chart of FIG. 15 is collected and concentrated to dryness to yield subject compound as a white powder-like material.

(4) Process for preparing 20-iso-O-methyl-condurango glycoside $D_o$ and condurango glycoside $D_o$ It is confirmed that subject compounds may be separated from Extract A and isolated by subjecting the latter to HPLC. But, this operation presents problems in view of commercial practicability because the presence of other polar similar materials cause the separation operation to be difficult and complex. But the subject two compounds are easily obtained by subjecting the above condurango glycoside $B_o$ to chemical reactions.

(i) Process for preparing 20-iso-O-methyl-condurango glycoside $D_o$

Condurango glycoside $B_o$ is subjected to alcoholysis and the resulting reaction solution is concentrated to dryness. The residue is subjected first to normal phase HPLC and then to reversed phase HPLC to isolate and purify subject compound.

As the solvent for the alcoholysis, a $10^{-6}$–$10^{-4}$ molar concentration, preferably a $10^{-4}$ molar concentration of acetic acid solution in methanol, a 0.001–0.01 N, preferably 0.005 N oxalic acid solution in methanol or the like is employed. The amount of the solvent used is 50–500 times (v/w) that of the starting material. The reaction time at room temperature may be 5–20 hours when a solution of acetic acid in methanol is employed or 30–60 minutes in case a solution of oxalic acid in methanol is used.

By following the normal phase HPLC operation, a fraction corresponding to Fr-6 fraction shown in the chart of FIG. 16 is collected. This fraction is then subjected to reversed phase HPLC operation to collect a fraction corresponding to Fr-6-1 fraction depicted in the chart of FIG. 17 which is then concentrated to dryness to yield subject compound as a white powder-like material.

(ii) Process for preparing condurango glycoside $D_o$

Condurango glycoside $B_o$ is subjected to hydrolysis, and then the resulting reaction solution is concentrated to dryness. The residue is subjected first to normal phase HPLC and then to reversed phase HPLC to isolate and purify subject compound.

The amount of the water used is 150–250 times (v/w) that of the starting material.

The hydrolysis may be effected at a temperature of from room temperature to 50° C., and a satisfactory result is obtained at room temperature without increasing the temperature. In the latter case, the reaction is completed after the solution is allowed to stand for 24–48 hours.

By following said normal phase HPLC operation, a fraction corresponding to Fr-7 fraction shown in the chart of FIG. 18 is collected. The obtained fraction is then treated by said reversed phase HPLC operation to collect a fraction corresponding to Fr-7-1 fraction shown in the chart of FIG. 19 which is then concentrated to dryness to yield subject compound as a white powder-like material.

In the foregoing procedures, 20-iso-O-methyl-condurango glycoside $D_o$ may be substituted for the condurango glycoside $B_o$ used as the starting material to yield subject compound.

The activity of the compounds of the present invention against Ehrlich carcinoma was confirmed by the screening test mentioned below.

Ehrlich carcinoma was employed for the determination of the antitumor properties, and the tumor to be tested was of subcutaneous solid type.

The animal group to which the compounds of the present invention were administered consisted of seven mice, whereas the control group consisted of ten mice.

Test method

Six weeks old ddy male mice (body weight: 28–30 g) were employed except for the case where condurango glycoside $A_o$ or $C_o$ was administered; in the latter case those weighing 20–26 g and being five weeks old were used.

The tumors were transplanted intraperitoneally in the mice. On the seventh day after the transplantation, the well grown cells of the tumors were taken out, and $1.5 \times 10^6$ cells ($3.0 \times 10^6$ cells in the case where condurango glycoside $A_o$ or $C_o$ was given) thereof was transplanted subcutaneously in the inguinal region of the mice to form solid tumors. At and after 24 hours after the transplantation, the compounds of the present invention dissolved in physiological saline solutions were administered to the mice intraperitoneally.

The volume of the respective solutions administered was 0.2 ml per mouse at one time, and the administration was continued for ten days at a rate of one time per day. Only physiological saline solutions were given to the mice of the control group.

On the thirtieth day after the transplantation, the tumors were taken out and measured to get the average weight of the tumors of the mice of the group to which the compounds of the present invention had been administered (T) and that of the control group (C) and to calculate the T/C (%).

| Compound administered | Results | | |
|---|---|---|---|
| | T/C (%) mg/kg × times | | |
| | 8 × 10 | 16 × 10 | 32 × 10 |
| Condurango glycoside $B_o$ | 23.3 | 11.8 | 10.0 |
| 20-O—methyl-condurango glycoside $D_o$ | 16.5 | 11.6 | — |
| Condurango glycoside $A_o$ | 32.1 | 27.3 | — |
| Condurango glycoside $C_o$ | — | 30.8 | 20.1 |
| 20-Iso-O—methyl-condurango glycoside $D_o$ | 38.1 | 26.3 | 18.0 |
| Condurango glycoside $D_o$ | 29.0 | 53.8 | 9.5 |

Next, the acute toxicity of the compounds of the present invention is as follows. In order to get data, the compounds of the present invention were administered to five weeks old ddy male mice (body weight: 21–25 g) intraperitoneally, and the general conditions, death cases and the change in the body weight were observed for five days after the administration.

| Compound administered | LD$_{50}$ (mg/kg) |
|---|---|
| Condurango glycoside $B_o$ | 615 |
| 20-O—methyl-condurango glycoside $D_o$ | 603 |
| Condurango glycoside $A_o$ | 75 |
| Condurango glycoside $C_o$ | 375 |
| 20-Iso-O—methyl-condurango glycoside $D_o$ | 642 |
| Condurango glycoside $D_o$ | 630 |

When the compounds of the present invention are employed in the form of solid preparations of oral administration, the preparations may be tablets, granules, powders, capsules or the like. The preparations may contain additives, for example, an excipient such as a saccharide or cellulose preparation, a binder such as starch paste or methyl cellulose, a filler, a disintegrator and so on, all being pharmaceutically commonly used additives and carriers. In case the compounds of the present invention are employed as oral liquid preparations, they may be of any form selected from aqueous preparations for internal use, suspensions, emulsions, syrups, etc. and further they may be in the form of dried products which are dissolved prior to the use.

The compounds of the present invention may also be injected in the form of aqueous solutions, suspensions or oily or aqueous emulsions, but usually the injections are prepared by dissolving or suspending them in aqueous liquid media such as sterile water or physiological saline solutions. If necessary, conventionally used dissolving agent, stabilizers, preservatives, additives for preparing isotonic solutions, etc. may be added to the injections.

The thus obtained injection preparations are administered intravenously, intramuscularly, subcutaneously or in any other appropriate manner. The dose level is increased or decreased appropriately depending on the conditions of disease, the age of the subject, the form of the preparation, the administration manner and so on in either case, whether the preparation is given orally or by injection, but the standard daily dose of the compounds of the present invention for adult subjects would be as follows:

| Compound administered | Administration route | |
|---|---|---|
| | Orally (mg/kg) | Parenterally (mg/kg) |
| Condurango glycoside $B_o$ | 0.2–100.0 | 0.2–16.0 |
| 20-O—methyl-condurango glycoside $D_o$ | 0.3–50.0 | 0.1–16.0 |
| Condurango glycoside $A_o$ | 0.6–6.0 | 0.2–2.0 |
| Condurango glycoside $C_o$ | 1.0–30.0 | 0.3–10.0 |
| 20-Iso-O—methyl-condurango glycoside $D_o$ | 0.6–51.0 | 0.2–17.0 |

| | Administration route | |
|---|---|---|
| Compound administered | Orally (mg/kg) | Parenterally (mg/kg) |
| Condurango glycoside $D_o$ | 0.6–51.0 | 0.2–17.0 |

BRIEF DESCRIPTION OF THE DRAWINGS

FIG. 1 shows a chart obtained when Extract A was subjected to normal phase analytical HPLC;

FIG. 2 shows a chart obtained when Extract A was subjected to normal phase HPLC;

FIG. 3 shows a chart obtained when the extract of Fr-2 fraction was subjected to normal phase HPLC;

FIG. 4 shows a chart obtained when Extract B-1 was subjected to normal phase analytical HPLC;

FIG. 5 shows a chart obtained when Extract B-2 was subjected to normal phase analytical HPLC;

FIG. 6 shows a chart obtained when the extract of Fr-3 fraction was subjected to reversed phase HPLC;

Figure 9:
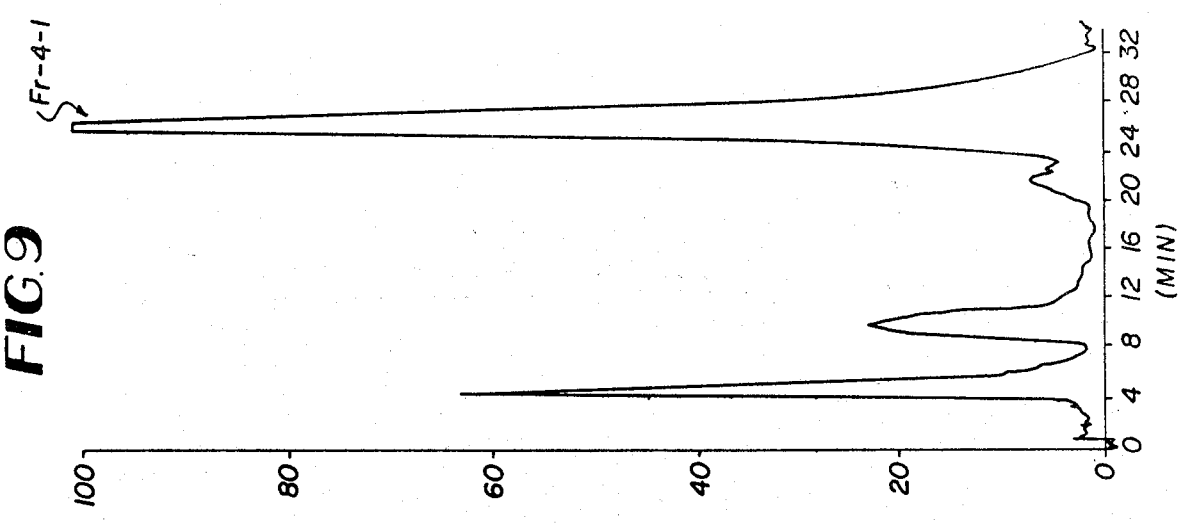
FIG. 9 shows a chart obtained when the extract of Fr-4 fraction was subjected to reversed phase HPLC.

(Best Mode for Carrying out the Invention)

Hereunder, the present invention will be explained in detail with reference to the example given below.

EXAMPLE

One liter of methanol was added to 500 g of finely divided bark of *Marsdenia cundurango* Reichenbach fil., and the mixture was allowed to stand at room temperature overnight. Then, the mixture was filtered, and the residue was treated three times in the same manner, each time using 0.75 l of methanol.

All the filtrates were combined, and then concentrated to dryness at 45° C. under reduced pressure to yield 69 g of an extract. To this extract transferred into a separatory funnel, there was added 150 ml of chloroform followed by vigorous shaking, and then the chloroform layer was obtained. To the residue, there was added 50 ml of chloroform to repeat the same operation as the above three times. All the chloroform extracts were combined and then subjected to suction filtration using Fibra Cel BH-40 (Johns Manville Co. Ltd.) as the filtration aid. The resulting filtrate was concentrated to dryness at 40° C. under reduced pressure to yield 42 g of an extract. This extract was dissolved in 50 ml of chloroform added thereto followed by the addition of 100 ml of n-hexane. The resulting mixture was well stirred and allowed to stand for 12 hours. Then, it was subjected to decantation to obtain the insoluble portion. This portion was dissolved in 25 ml of chloroform, and 50 ml of n-hexane was added to the resulting solution which was then well stirred and allowed to stand for 2 hours. The solution was subjected to decantation to obtain the insoluble portion and then treated in the same way as in the above three times. The finally obtained insoluble portion was concentrated to dryness at 45° C. under reduced pressure and crushed to yield 18 g of a brown powder-like material (Extract A). Twenty milligrams of the Extract A was dissolved in 10 ml of chloroform, and the resulting solution was subjected to normal phase analytical HPLC [filler: silica gel (Wakogel LC-5H, manufactured by Wako Junyaku Industry Co., Ltd., totally porous crushed type, 5 $\mu$m); column: i.d.$\times$1.=4 mm$\times$200 mm; eluant: n-hexane/chloroform/methanol mixture (volumetric ratio=7:2:1); flow rate: 1.5 ml/min.; pressure: 30 kg/cm$^2$; and detection: at UV 280 nm (0.64 AUFS)]. The obtained data is shown in the chart depicted in FIG. 1.

The thus obtained 18 g of Extract A was dissolved in 50 ml of chloroform in 6 g portions. Then, n-hexane was added to the resulting mixture in the maximum but non-turbidity-causing amount, and the resulting solution was subjected to normal phase HPLC [System 500 manufactured by Waters Co., Ltd., filler: Preppak 500-Silica (Manufactured by Waters Co., Ltd., totally porous silica gel, spherical, surface area=320 m$^2$/g); column: i.d.$\times$1.=57 mm$\times$300 mm; eluant: n-hexane/chloroform/methanol mixture (volumetric ratio=6:3:1); flow rate: 150 ml/min; and detection: at RI (1/20$\times$10$^{-4}$ RIUFS)]. An eluate chosen on the basis of the peak corresponding to Fr-2 fraction shown in FIG. 2 and another eluate chosen on the basis of the peak corresponding to Fr-3 fraction shown in the same figure were collected for 12 and 13 minutes, respectively. The respective eluates were concentrated to dryness at 45° C. under reduced pressure to provide 5.54 g of an extract from Fr-2 fraction and 2.88 g of an extract from Fr-3 fraction, respectively.

The extract from Fr-2 fraction was dissolved in 50 ml of chloroform followed by the addition of n-hexane in the maximum but non-turbidity-causing amount. This resulting solution was subjected to normal phase HPLC under the same conditions as the above, but using an n-hexane/chloroform/methanol mixture (volumetric ratio=6:1:1) as the eluant. An eluate chosen on the basis of the peak corresponding to Fr-2-1 fraction shown in FIG. 3 and another eluate chosen on the basis of the peak corresponding to Fr-2-2 fraction shown in the same figure were collected for 6.5 minutes and 8 minutes, respectively.

The respective eluates were concentrated to dryness at 45° C. under reduced pressure to yield 1.98 g of a white powder-like extract (Extract B-1 corresponding to Fr-2-1 fraction) and 0.91 g of another white powder-like extract (Extract B-2 corresponding to Fr-2-2 fraction), respectively.

The data obtained by subjecting the obtained Extracts B-1 and B-2 to normal phase analytical HPLC under the same conditions as for Extract A, respectively, is shown in FIGS. 4 and 5 of the accompanying drawings, respectively.

Separately, the extract from Fr-3 fraction was dissolved in 50 ml of a 70% (v/v) aqueous methanol solution and subjected to reversed phase HPLC [System 500 manufactured by Waters Co., Ltd.; filler: Preppak 500-C18 (manufactured by Waters Co., Ltd., chemically bonded silica gel-$C_{18}$ type); column: i.d.$\times$1.=57 mm$\times$300 mm; eluant: 70% (v/v) aqueous methanol solution; flow rate: 100 ml/min; and detection: at RI (1/50$\times$10$^{-4}$ RIUFS)].

An eluate chosen on the basis of the peak corresponding to Fr-3-1 fraction shown in FIG. 6 was collected for 12 minutes and concentrated to dryness at 45° C. under reduced pressure to yield 0.88 g of a white powder-like extract (Extract B-3).

Figure 7:
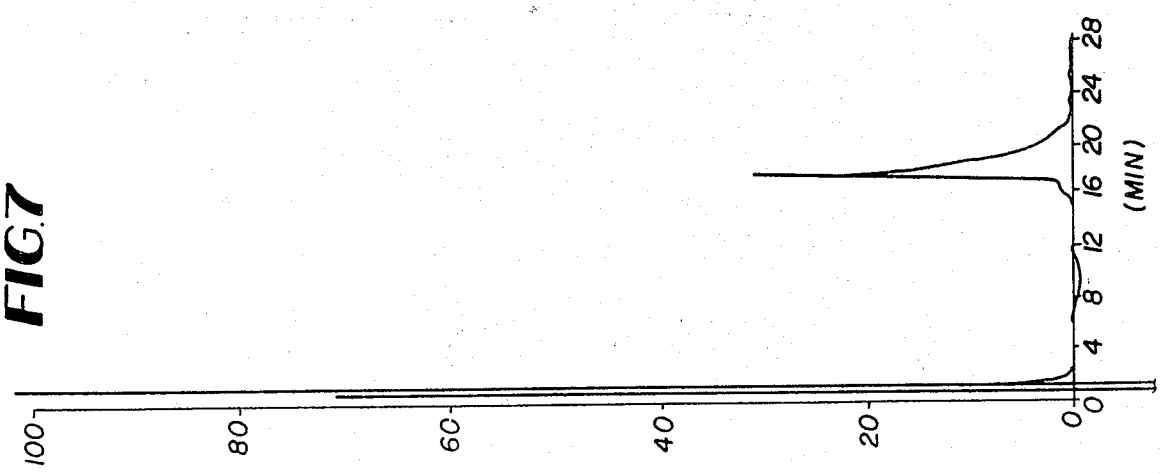
FIG. 7 shows a chart obtained when Extract B-3 was subjected to normal phase analytical HPLC.

The data obtained by subjecting the thus obtained Extract B-3 to normal phase analytical HPLC under the same conditions as for Extract A is shown in the chart depicted in FIG. 7.

The object novel compounds of the present invention were obtained using Extracts B-1, B-2 and B-3 from the foregoing operations as follows:

Condurango glycoside $B_o$

Extract B-1 was dissolved in 1 ml of an acetonitrile/water/diethylamine mixture (volumetric ratio=48:51.975:0.025) in 60 mg portions, and the resulting solution was subjected to reversed phase HPLC [filler: Lichrosorb RP-8 (manufactured by Merck Co., Ltd., chemically bonded silica gel-$C_8$ type, 5 $\mu$m); column: i.d.$\times$1.=8 mm$\times$250 mm; eluant: acetonitrile/water/diethylamine mixture (volumetric ratio=48:51.975:0.025); flow rate: 1.8 ml/min.; pressure: 150 kg/cm$^2$; and detection: at RI (64$\times$10$^{-6}$ RIUFS)]. Eluates chosen on the basis of the peak corresponding to Fr-4 fraction shown in FIG. 8 were collected for 5 minutes, combined and concentrated to dryness at 45° C. under reduced pressure.

The residue was subjected to the same operation as the above, and eluates chosen on the basis of the peak corresponding to Fr-4-1 fraction shown in FIG. 9 were collected for 5 minutes, combined and concentrated to dryness at 45° C. under reduced pressure to yield 160 mg of a white powder-like extract.

Figure 10:
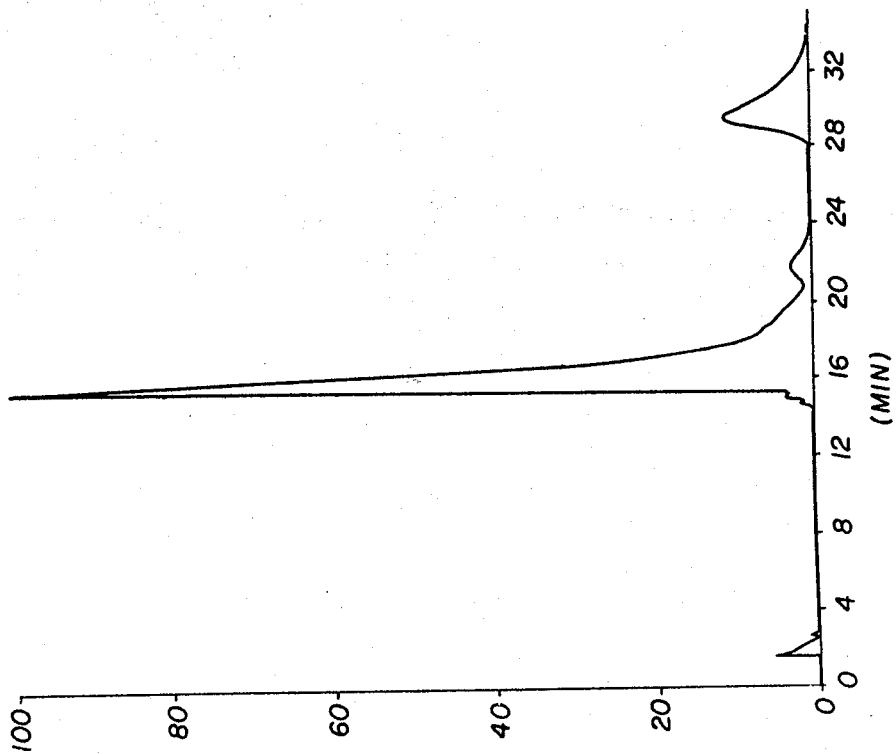
FIG. 10 shows a chart obtained when the extract of Fr-4-1 fraction was subjected to normal phase HPLC.

This extract was dissolved in 1 ml of chloroform in 10 mg portions, and then subjected to normal phase HPLC [filler: silica gel (Wako-gel LC-5H manufactured by Wako Junyaku Industry Co., Ltd. in Japan, totally porous crushed type, 5 $\mu$m); column: i.d.$\times$1.=8 mm$\times$250 mm; eluant: n-hexane/chloroform/methanol mixture (volumetric ratio: 7:2:1); flow rate: 5 ml/min.; pressure: 40 kg/cm$^2$; and detection: at UV 280 nm (1.28 AUFS)]. Eluates chosen on the basis of the one peak shown in FIG. 10 were collected for 2 minutes, combined and concentrated to dryness at 45° C. under reduced pressure to yield 85 mg of condurango glycoside $B_o$ as a white powder-like material.

This material had the following physicochemical properties:

(1) M.P.: 170°–180° C. (white non-crystalline solid).

(2) Specific rotation: $[\alpha]_D^{20}=+11.5°$ (C=0.72 in CHCl$_3$).

(3) Analysis ($C_{59}H_{86}O_{22}.2H_2O$): Calculated, (%): C; 59.88, H; 7.67. Found, (%): C; 59.72, H; 7.48.

(4) UV$\lambda_{max}^{EtOH}$, nm ($\epsilon$): 217 (3.27$\times$10$^4$), 222 (3.04$\times$10$^4$) and 280 (5.05$\times$10$^4$).

(5) IR$\nu_{max}^{CHCl_3}$, cm$^{-1}$: 3350, 1735, 1710, 1640, 1600, 1580, 1500, 1060–1100, 1000, 900 and 845.

(6) $^1$H-NMR(CDCl$_3$)$\delta$, ppm: 1.00 (3H, S, 19Me), 1.23 (3H, d, J=6 Hz), 1.27 (3H, d.J=6 Hz), 1.36 (3H, d, J=6 Hz), 1.40 (3H, S, 21Me), 1.92 (3H, S, Ac), 3.40, 3.46, 3.62 (each 3H, S), 4.15 (1H, broad d, J=8 Hz), 4.45 (2H, m), 4.83 (2H, broad d, J=8 Hz), 5.12 (1H, t, J=9 Hz), 5.21 (1H, d, J=6 Hz), 6.39 and 7.70 (2H, ABq, J=16 Hz) and 7.44–7.56 (5H, m).

(7) $^{13}$C-NMR (Py-d$_5$), ppm Genin portions: 79.3 (3-C), 112.8 (20-C), 90.1 (14-C), 117.9, 128.7 (two lines overlapped), 129.3 (two lines overlapped), 130.8, 134.7, 146.1 and 166.1 (each is of cynnamoyl carbon) and 170.4 (carbonyl carbon of acetyl group) Sugar portions: 96.1, 101.7, 101.8 and 106.4 (1-C of the respective sugars).

20-O-methyl-condurango glycoside $D_o$

Figure 8:
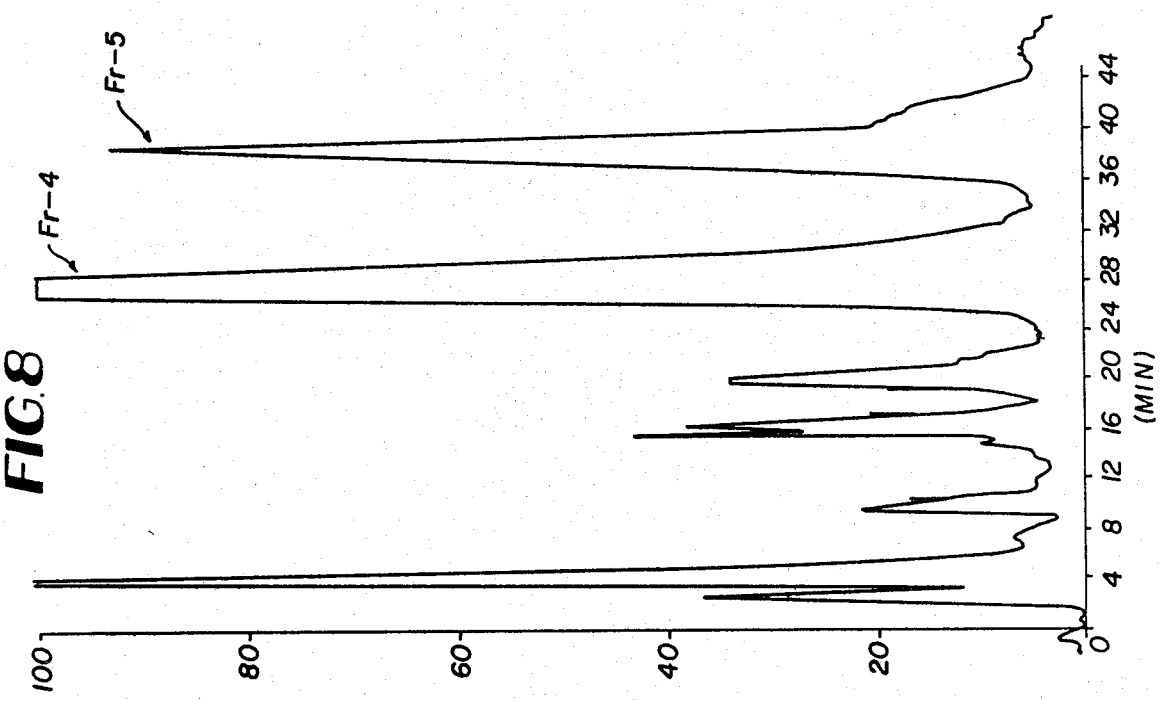
FIG. 8 shows a chart obtained when Extract B-1 was subjected to reversed phase HPLC.

The fraction coming after the fraction of condurango glycoside $B_o$ in the first reversed phase HPLC operation effected for the above fractionation of condurango glycoside $B_o$, namely, eluates chosen on the basis of the peak corresponding to Fr-5 fraction shown in FIG. 8 were collected for 4 minutes, combined and concentrated to dryness at 45° C. under reduced pressure.

Figure 11:
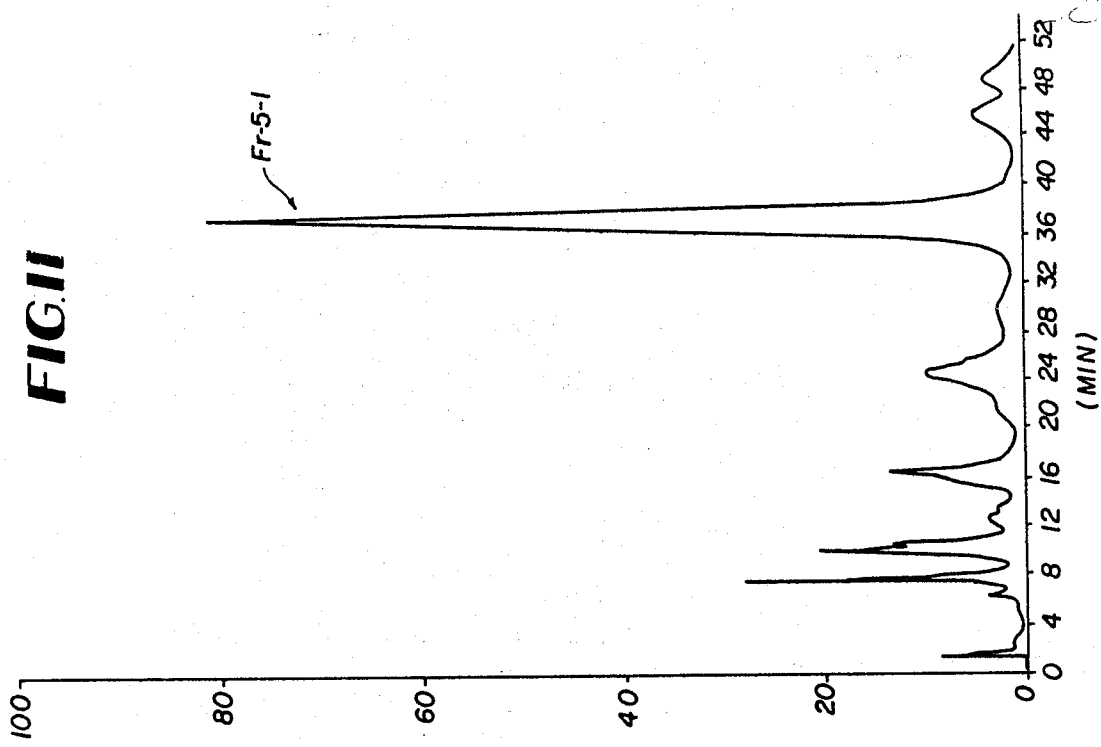
FIG. 11 shows a chart obtained when the extract of Fr-5 fraction was subjected to reversed phase HPLC.

The residue was subjected to the same operation as the above, and eluates chosen on the basis of the peak corresponding to Fr-5-1 fraction shown in FIG. 11 were collected for 3 minutes, combined and concentrated to dryness at 45° C. under reduced pressure to yield 110 mg of a white powder-like extract.

Figure 12:
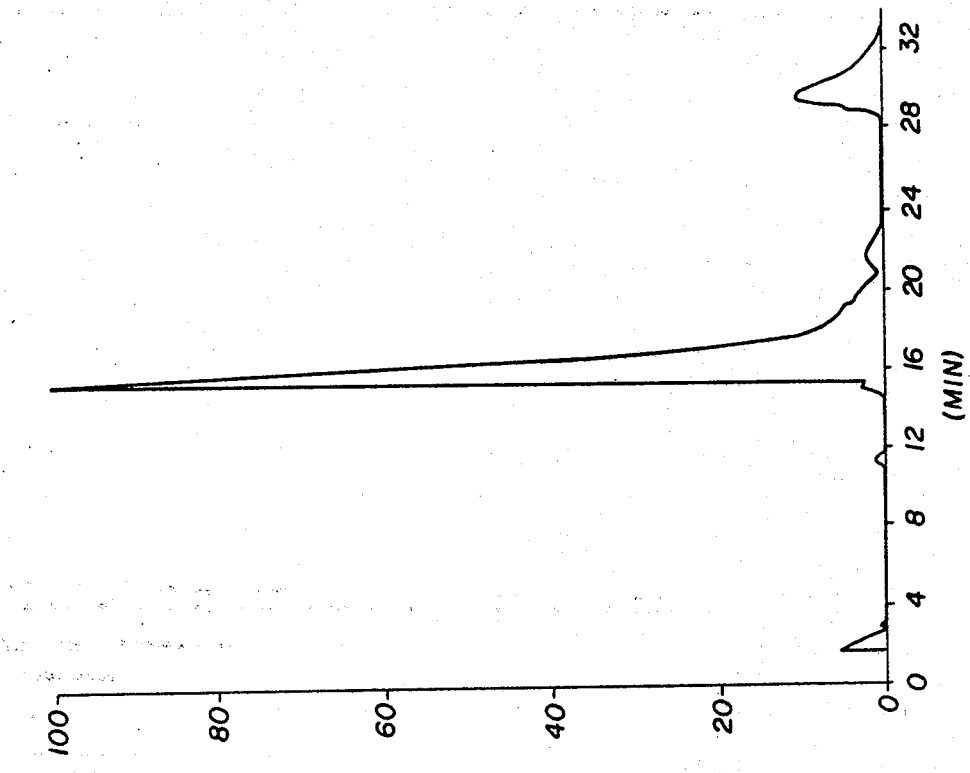
FIG. 12 shows a chart obtained when the extract of Fr-5-1 fraction was subjected to normal phase HPLC.

This extract was dissolved in 1 ml of chloroform in 10 mg portions, and then subjected to normal phase HPLC under the same conditions as for the above fractionation of condurango glycoside $B_o$. Eluates chosen on the basis of the one peak shown in FIG. 12 were collected for 2 minutes, combined and concentrated to dryness at 45° C. under reduced pressure to yield 72 mg of 20-O-methyl-condurango glycoside $D_o$ as a white powder-like material.

This material had the following physicochemical properties:

(1) M.P.: 180°–190° C. (white non-crystalline solid)

(2) Specific rotation: $[\alpha]_D^{20}=-8.76°$ (C=0.72 in CHCl$_3$)

(3) Analysis ($C_{60}H_{90}O_{23}.4H_2O$): Calculated, (%): C; 57.59, H; 7.89. Found, (%): C; 57.97, H; 7.39.

(4) UV$\lambda_{max}^{EtOH}$, nm ($\epsilon$): 217 (2.10$\times$10$^4$), 222 (1.92$\times$10$^4$) and 280 (3.11$\times$10$^4$).

(5) IR$\nu_{max}^{CHCl_3}$, cm$^{-1}$: 3350, 1735, 1710, 1635, 1600, 1580, 1500, 1160, 1100, 960, 905 and 880.

(6) $^1$H-NMR(CDCl$_3$) $\delta$, ppm: 0.86 (3H, S, 19Me), 1.22 (3H, d, J=6 Hz), 1.24 (6H, d, J=6 Hz), 1.38 (3H, S, 21Me), 1.88 (3H, S, Ac), 3.27, 3.37, 3.43, 3.59 (each 3H, S), 4.09 (2H, ABq, J=9 Hz, C-18), 4.42 (2H, m), 4.81 (2H, m), 5.03 (2H, m), 5.38 (1H, S, OH), 6.44 and 7.73 (2H, ABq, J=16 Hz) and 7.40–7.52 (5H, m).

(7) $^{13}$C-NMR (Py-d$_5$), ppm Genin portions: 79.3 (3-C), 106.0 (20-C), 81.1 (14-C), 117.8, 128.7 (two lines overlapped), 129.9 (two lines overlapped), 130.9, 134.4, 146.4 and 166.9 (each is of cynnamoyl carbon) and 170.0 (carbonyl carbon of acetyl group) Sugar portions: 96.1, 101.7, 101.9 and 106.4 (1-C of the respective sugars).

Condurango glycoside A$_o$

Figure 13:
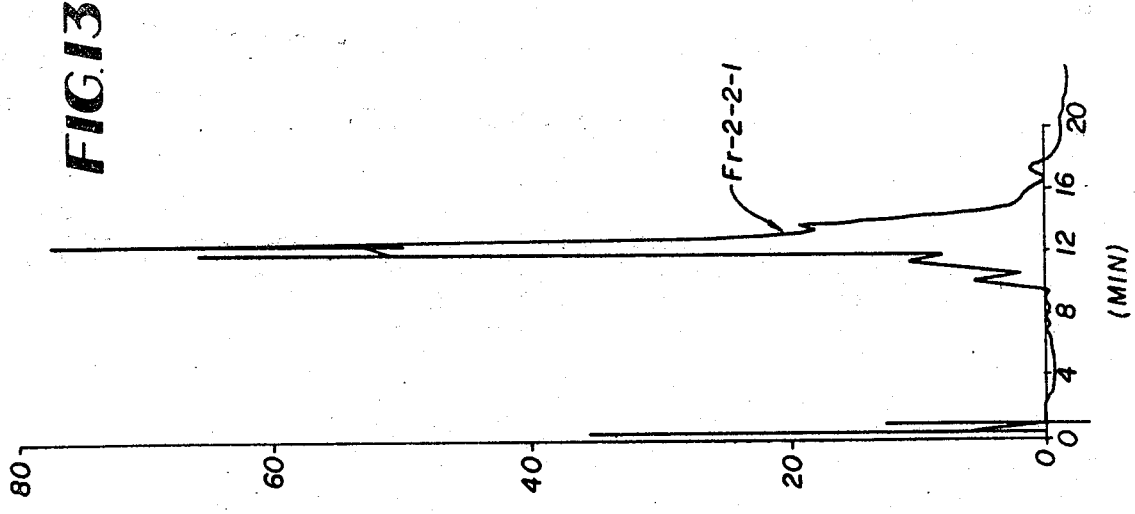
FIG. 13 shows a chart obtained when Extract B-2 was subjected to normal phase HPLC.

Extract B-2 was dissolved in 1 ml of chloroform in 10 mg portions, and then subjected to normal phase HPLC [filler: silica gel (Wako-gel LC-5H manufactured by Wako Junyaku Industry Co., Ltd. in Japan, totally porous crushed type, 5 μm); column: i.d.×1.=8 mm×250 mm; eluant: n-hexane/chloroform/methanol mixture (volumetric ratio=7:2:1); flow rate: 6 ml/min.; pressure: 50 kg/cm$^2$; and detection: at UV 250 nm (0.64 AUFS)]. Eluates chosen on the basis of the one peak shown in FIG. 13 (Fr-2-2-1 fraction) were collected for 2 minutes, combined and concentrated to dryness at 45° C. under reduced pressure to yield 700 mg of a white powder-like extract.

Figure 14:
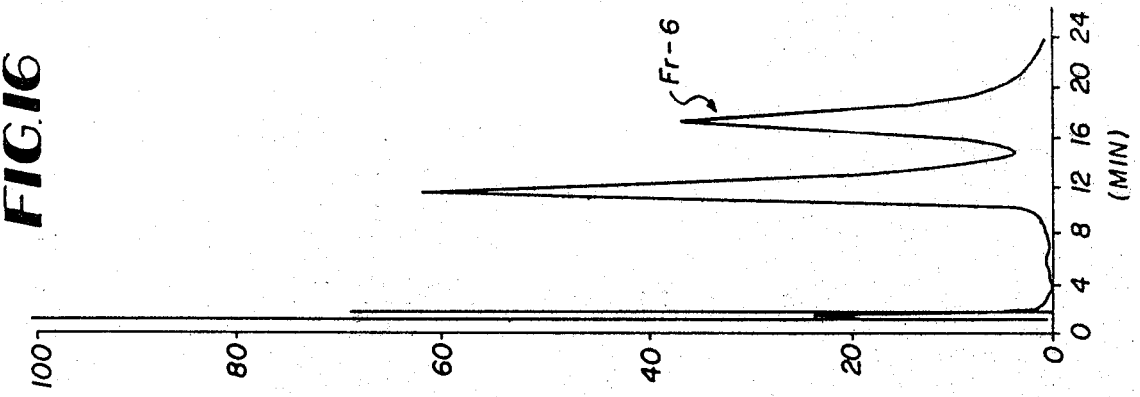
FIG. 14 shows a chart obtained when the extract of Fr-2-2-1 fraction was subjected to reversed phase HPLC.

This extract was dissolved in 20 ml of a 75% (v/v) aqueous methanol solution in 10 mg portions, and the resulting solution was subjected to reversed phase HPLC [filler: Lichorsorb RP-8 (manufactured by Merck Co., Ltd., 5 μm); column: i.d.×1.=8 mm×250 mm; eluant: 75% (v/v) aqueous methanol solution; flow rate: 4 ml/min.; pressure: 160 kg/cm$^2$; and detection: at UV 280 nm (1.28 AUFS)]. Eluates chosen on the basis of the one peak shown in FIG. 14 were collected for 2 minutes, combined and concentrated to dryness at 45° C. under reduced pressure to yield 466 mg of white powder-like condurango glycoside A$_o$.

This material had the following physicochemical properties:

(1) M.P.: 170°–174° C. (white non-crystalline solid).

(2) Specific rotation: $[\alpha]_D^{20} = +43.9°$ (C=0.615 in MeOH).

(3) Analysis ($C_{59}H_{88}O_{22}.3H_2O$): Calculated, (%): C; 58.89, H; 7.87. Found, (%): C; 59.23, H; 7.69.

(4) UV$\lambda_{max}^{MeOH}$, nm ($\epsilon$): 217 (2.33×10$^4$), 223 (2.10×10$^4$) and 280 (3.39×10$^4$).

(5) IR$\nu_{max}^{Nujol}$, cm$^{-1}$: 3350, 1740, 1700, 1630, 1255, 1235, 1140, 1070, 870 and 820.

(6) $^1$H-NMR(CDCl$_3$) δ, ppm: 0.96 (3H, S, 19Me), 1.11 (3H, S, 18Me), 1.23 (3H, d, J=6 Hz), 1.25 (3H, d, J=6 Hz), 1.29 (3H, d, J=6 Hz), 1.86 (3H, S, Ac), 2.15 (3H, S, 21Me), 3.39, 3.44, 3.61 (each 3H, S), 4.80 (1H, d, J=10 Hz), 5.34 (1H, t, J=10 Hz), 6.46 and 7.78 (2H, ABq, J=16 Hz) and 7.45–7.60 (5H, m).

(7) $^{13}$C-NMR (Py-d$_5$), ppm Genin portions: 79.3 (3-C), 83.9 (14-C), 213.6 (20-C), 118.0, 128.7 (two lines overlapped), 129.3 (two lines overlapped), 130.9, 134.7, 146.3 and 166.9 (each is of cynnamoyl carbon) and 170.3 (carbonyl carbon of acetyl group) Sugar portions: 96.1, 101.7, 101.8 and 106.4 (1-C of the respective sugars).

Condurango glycoside C$_o$

Extract B-3 was dissolved in 1 ml of a 50% (v/v) aqueous acetonitrile solution in 20 mg portions, and the resulting solution was subjected to reversed phase HPLC [filler: Lichrosorb RP-8 (manufactured by Merck Co., Ltd., 5 μm); column: i.d.×1.=8 mm×250 mm; eluant: 50% (v/v) aqueous acetonitrile solution; flow rate: 4 ml/min.; pressure: 150 kg/cm$^2$; and detection: at UV 250 nm (0.64 AUFS)]. Eluates chosen on the basis of the one peak shown in FIG. 15 were collected for 2 minutes, combined and concentrated to dryness at 40° C. under reduced pressure to yield 700 mg of white powder-like condurango glycoside C$_o$.

This material had the following physicochemical properties:

(1) M.P.: 160°–170° C. (white non-crystalline solid).

(2) Specific rotation: $[\alpha]_D^{20} = +25.9°$ (C=1.28 in MeOH).

(3) Analysis ($C_{59}H_{90}O_{22}.2H_2O$): Calculated, (%): C; 59.68, H; 7.98. Found, (%): C; 59.31, H; 7.71.

(4) UV$\lambda_{max}^{MeOH}$, nm ($\epsilon$): 216 (2.83×10$^4$), 222 (2.52×10$^4$) and 279 (3.67×10$^4$).

(5) IR$\nu_{max}^{Nujol}$, cm$^{-1}$: 3350, 1740, 1710, 1630, 1260, 1160, 1060, 870 and 820.

(6) $^1$H-NMR(CDCl$_3$) δ, ppm: 0.96 (3H, S, 19Me), 1.33 (3H, S, 18Me) ca 1.24 (4×3H, m), 1.85 (3H, S, Ac), 3.38, 3.44, 3.60 (each 3H, S), 4.40 (1H, broad d, J=8 Hz), 4.50 (1H, broad d, J=9 Hz), 4.86 (1H, d, J=10 Hz), 5.36 (1H, t, J=10 Hz), 6.48 and 7.78 (2H, ABq, J=16 Hz) and 7.45–7.60 (5H, m).

(7) $^{13}$C-NMR (Py-d$_5$), ppm Genin portions: 71.9 (20-C), 79.2 (3-C), 83.4 (14-C), 118.6, 128.6 (two lines overlapped), 129.2 (two lines overlapped), 130.9, 134.8, 145.6 and 167.0 (each is of cynnamoyl carbon) and 170.4 (carbonyl carbon of acetyl group) Sugar portions: 96.0, 101.8 (two lines overlapped) and 106.5 (1-C of the respective sugars).

20-Iso-O-methyl-condurango glycoside D$_o$

Condurango glycoside B$_o$ (100 mg) was dissolved in 50 ml of a 10$^{-4}$ molar solution of acetic acid in methanol, and the resulting solution was allowed to stand at room temperature for 20 hours and then concentrated to dryness at 45° C. under reduced pressure.

Figure 16:
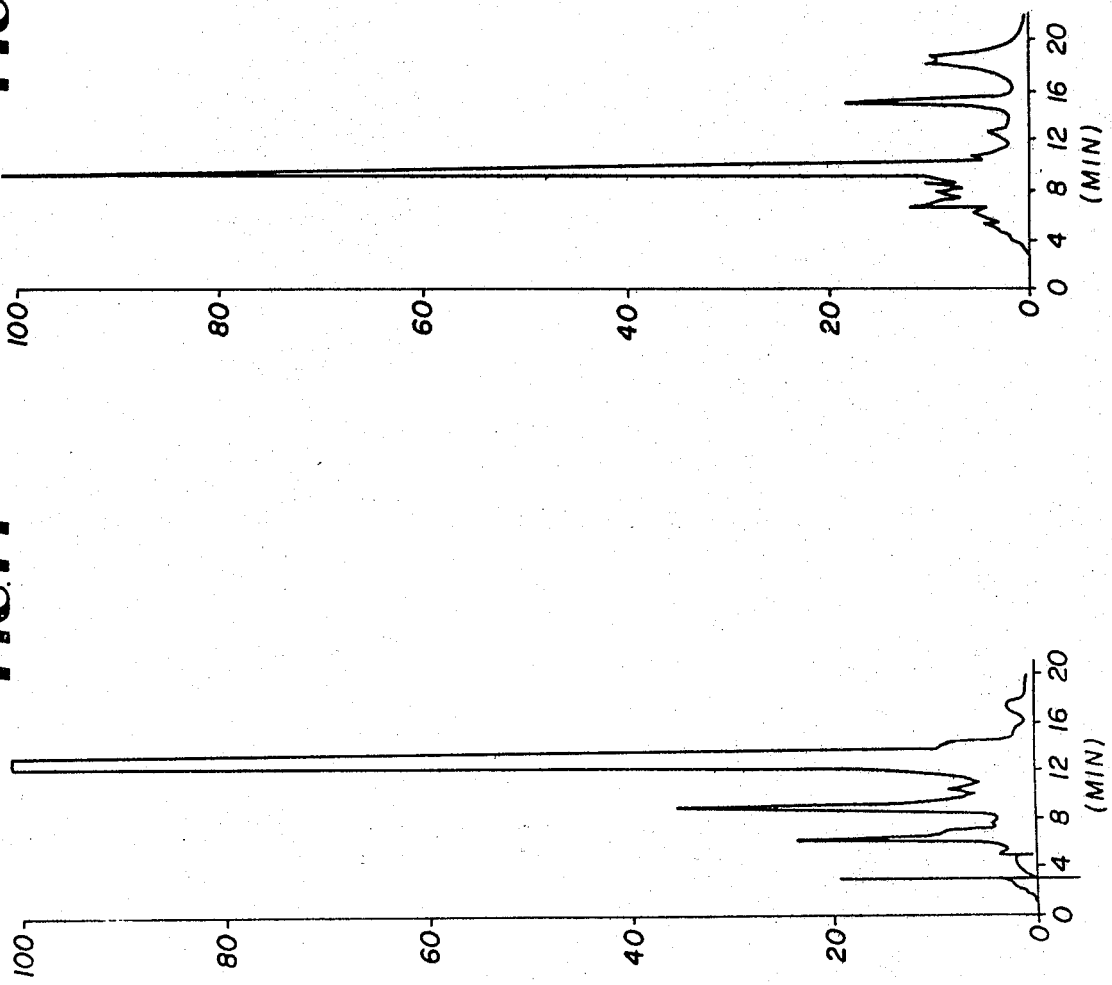
FIG. 16 shows a chart obtained when condurango glycoside $B_o$ after alcoholysis was subjected to normal phase HPLC.

The resulting residue (100 mg) was dissolved in 5 ml of chloroform and then subjected to normal phase HPLC [filler: silica gel (Wako-gel LC-5H manufactured by Wako Junyaku Industry Co., Ltd. in Japan, totally porous crushed type, 5 μm); column: i.d.×1.=8 mm×250 mm; eluant: n-hexane/chloroform/methanol mixture (volumetric ratio=7:2:1); flow rate: 6 ml/min.; pressure: 35 kg/cm$^2$; and detection: at RI (64×10$^{-6}$ RIUFS)]. Eluates chosen on the basis of the peak corresponding to Fr-6 fraction shown in FIG. 16 were collected for 4 minutes, combined and concentrated to dryness at 45° C. under reduced pressure to yield 50 mg of white powder.

Figure 17:
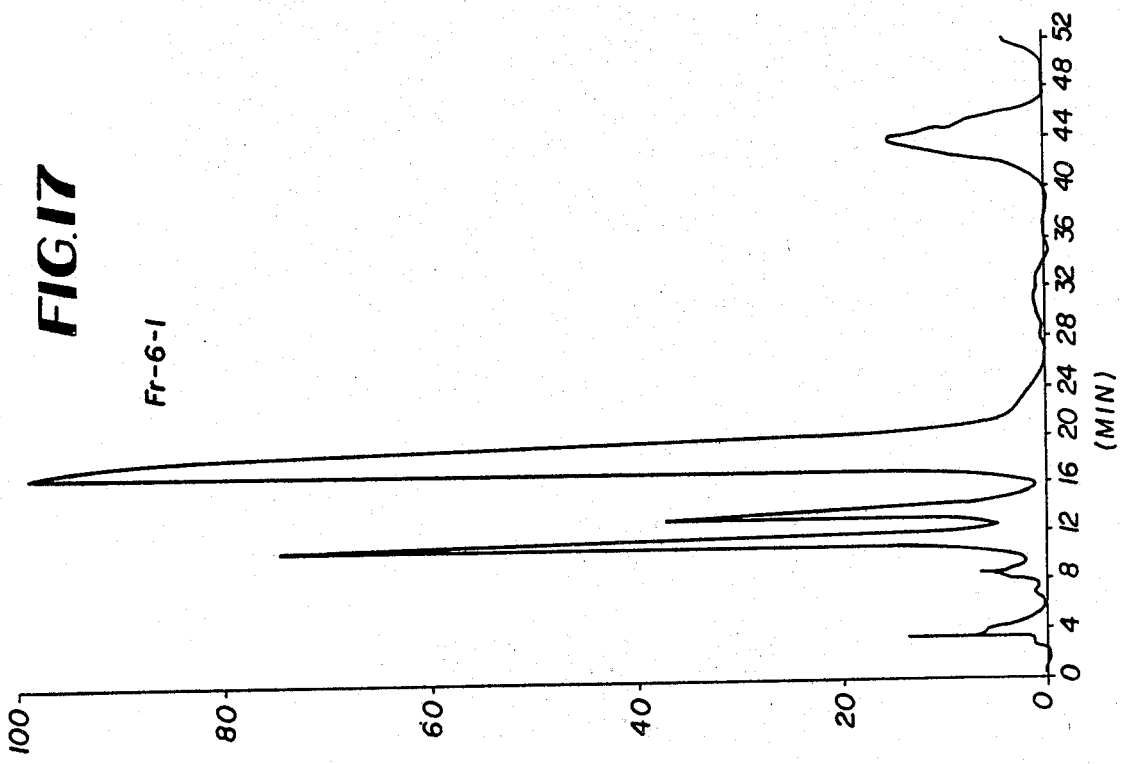
FIG. 17 shows a chart obtained when the extract of Fr-6 fraction was subjected to reversed phase HPLC.

The powder was dissolved in 2 ml of a 48% (v/v) aqueous acetonitrile solution, and the resulting solution was subjected to reversed phase HPLC [filler: Lichrosorb RP-18 (manufactured by Merck Co., Ltd., chemically bonded silica gel-C$_{18}$ type, 5 μm): column: i.d.×1.=8 mm×250 mm; eluant: 48% (v/v) aqueous acetonitrile solution; flow rate: 24 ml/min.; pressure: 170 kg/cm$^2$; and detection: at RI (64×10$^{-6}$ RIUFS)]. Eluates chosen on the basis of the peak corresponding to Fr-6-1 fraction shown in FIG. 17 were collected for 3 minutes, combined and concentrated to dryness at 45° C. under reduced pressure to yield 30 mg of white powder-like 20-iso-O-methyl-condurango glycoside D$_o$.

This material had the following physicochemical properties:

(1) M.P.: 168°–173° C. (white non-crystalline solid).

(2) Specific rotation: $[\alpha]_D^{20} = -19.0°$ (C=1.46 in MeOH).

(3) Analysis ($C_{60}H_{90}O_{23}.4H_2O$): Calculated, (%): C; 57.59; H; 7.89. Found, (%): C; 57.67; H; 7.42.

(4) UV$\lambda_{max}^{EtOH}$, nm ($\epsilon$): 218 (2.30×10$^4$), 224 (2.10×10$^4$) and 280 (3.30×10$^4$).

(5) IR$\nu_{max}^{CHCl_3}$, cm$^{-1}$: 3400, 1735, 1710, 1635, 1600, 1580, 1500, 1060–1100 and 950.

(6) $^1$H-NMR (CDCl$_3$) δ, ppm: 1.00 (3H, s, 19Me), 1.20–1.35 (9H, m) 1.40 (3H, s. 21Me), 1.90 (3H, s, Ac), 3.29, 3.35, 3.41, 3.56 (each 3H, s) and 6.35 and 7.66 (2H, ABq, J=16 Hz), 7.40 (5H, m).

(7) $^{13}$C-NMR (Py-d$_5$), ppm Genin portions: 79.3 (3-C), 83.3 (14-C), 109.4 (20-C), 118.7, 128.5 (two lines overlapped), 129.2 (two lines overlapped), 130.6, 134.8, 145.5 and 166.1 (each is of cynnamoyl carbon) and 169.3 (carbonyl carbon of acetyl group) Sugar portions: 96.2, 101.7, 101.8 and 106.4 (1-C of the respective sugars).

Condurango glycoside D$_o$

Figure 18:
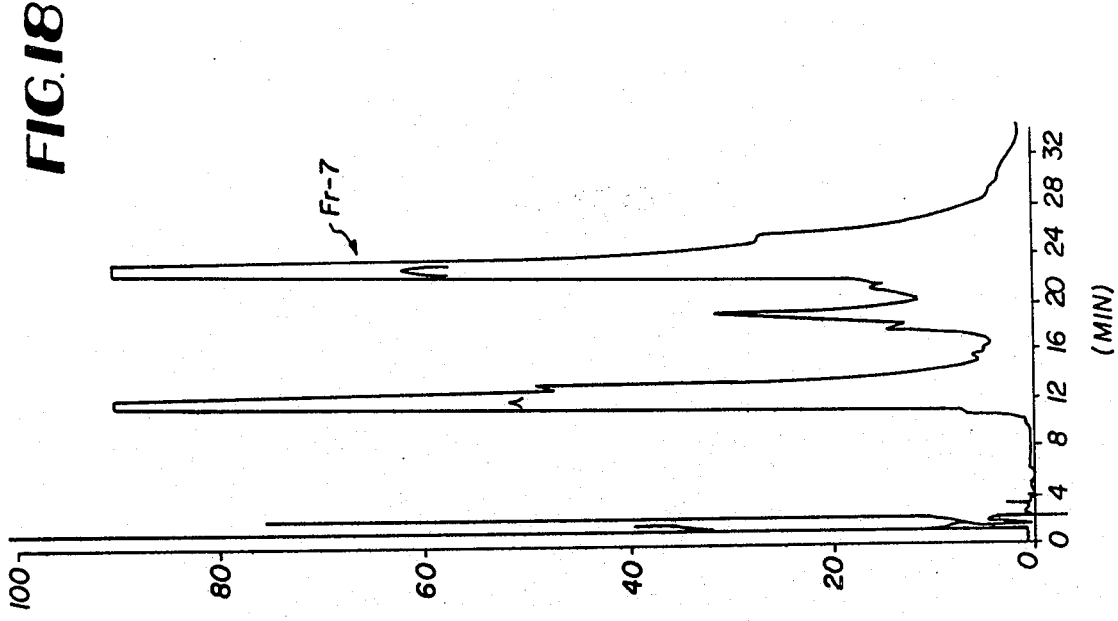
FIG. 18 shows a chart obtained when condurango glycoside $B_o$ after hydrolysis was subjected to normal phase HPLC.

Condurango glycoside B$_o$ (100 mg) was dissolved in 20 ml of water, and the resulting solution was allowed to stand at room temperature for 24 hours and then concentrated to dryness at 45° C. under reduced pressure. The resulting residue (100 mg) was dissolved in 2 ml of chloroform and subjected to normal phase HPLC [filler: silica gel (Wako-gel LC-5H manufactured by Wako Junyaku Industry Co., Ltd. in Japan, totally porous crushed type, 5 μm); column: i.d.×1.=8 mm×250 mm; eluant: n-hexane/chloroform/methanol mixture (volumetric ratio=7:2:1); flow rate: 6 ml/min.; pressure: 35 kg/cm$^2$; and detection: at RI (64×10$^{-6}$ RI-UFS)]. Eluates chosen on the basis of the peak corresponding to Fr-7 fraction shown in FIG. 18 were collected for 2 minutes, combined and concentrated to dryness at 45° C. under reduced pressure to yield 43 mg of white powder.

Figure 19:
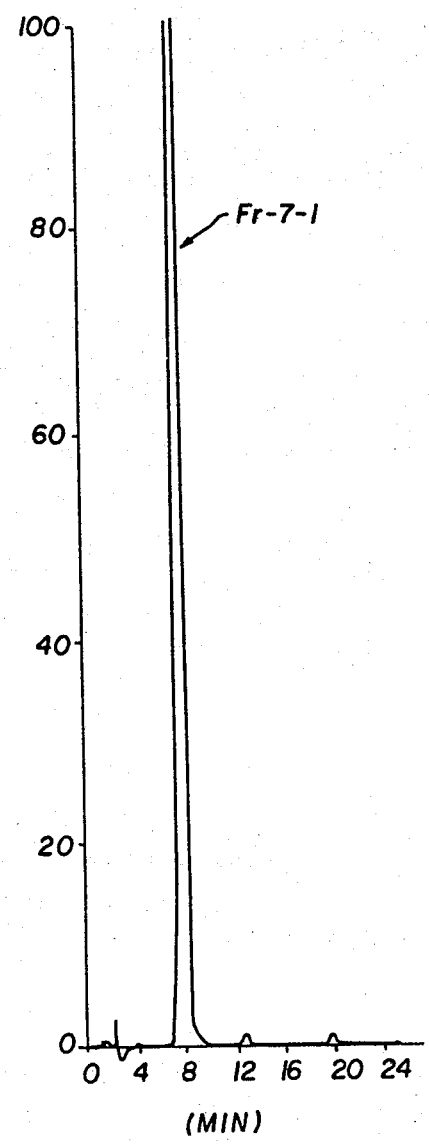
FIG. 19 shows a chart obtained when the extract of Fr-7 fraction was subjected to reversed phase HPLC.

The powder was dissolved in 2 ml of a 50% (v/v) aqueous acetonitrile solution, and the resulting solution was subjected to reversed phase HPLC [filler: Lichrosorb RP-18 manufactured by Merck Co., Ltd., 5 μm); column: i.d.×1.=8 mm×250 mm; eluant: 50% (v/v) aqueous acetonitrile solution; flow rate: 2.4 ml/min.; pressure: 150 kg/cm$^2$; and detection: at RI (32×10$^{-6}$ RIUFS)]. Eluates chosen on the basis of the peak corresponding to Fr-7-1 fraction shown in FIG. 19 were collected for 1 minute and 20 seconds, combined and concentrated to dryness at 45° C. under reduced pressure to yield 30 mg of white powder-like condurango glycoside D$_o$.

This material had the following physicochemical properties:

(1) M.P.: 183°-188° C. (white non-crystalline solid).

(2) Specific rotation: [α]$_D^{20}$=+13.5° (C=0.99 in MeOH).

(3) Analysis (C$_{59}$H$_{88}$O$_{23}$.4H$_2$O): Calculated, (%): C; 57.27, H; 7.82. Found, (%): C; 57.11, H; 7.36.

(4) UVλ$_{max}^{EtOH}$, nm (ε): 218 (1.54×10$^4$), 221 (1.40×10$^4$) and 280 (2.29×10$^4$).

(5) IRν$_{max}^{CHCl_3}$, cm$^{-1}$: 3400, 1735, 1710, 1635, 1600, 1500, 1160, 900 and 860.

(6) $^1$H-NMR (CDCl$_3$)δ, ppm: 1.00 (3H, S, 19Me), 1.20-1.35 (9H, m), 1.40 (3H, S. 21Me), 1.90 (3H, S. Ac), 3.38, 3.43, 3.49 (each 3H, S), 6.36 and 7.68 (2H, ABq, J=16 Hz) and 7.36 (5H, m).

(7) $^{13}$C-NMR (Py-d$_5$), ppm: Genin portions: 79.3 (3-C), 81.8 (14-C), 103.8 (20-C), 118.0, 128.6 (two lines overlapped), 129.1 (two lines overlapped), 130.0, 134.7, 146.2 and 166.8 (each is of cynnamoyl carbon), 170.0 (carbonyl carbon of acetyl group) Sugar portions: 96.1, 101.6, 101.7 and 106.3 (C-1 of the respective sugars).

We claim:

1. Condurango glycoside compounds represented by the general formula (I):

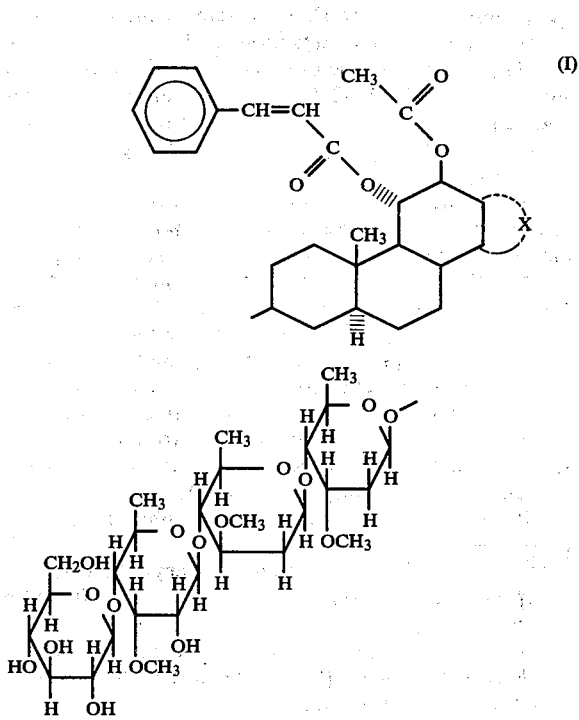

(where X together with the 13 and 14 position carbon atoms is a group selected from the group consisting of

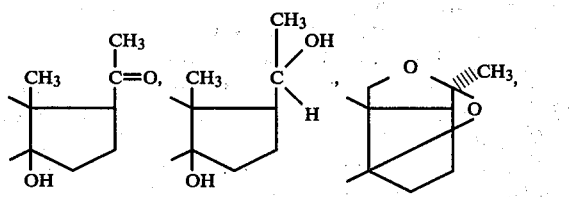

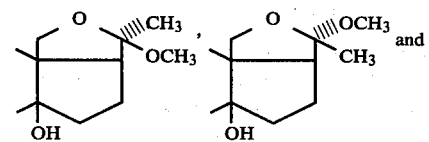

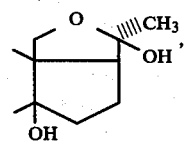

2. A process for preparing condurango glycoside B$_o$ represented by the formula:

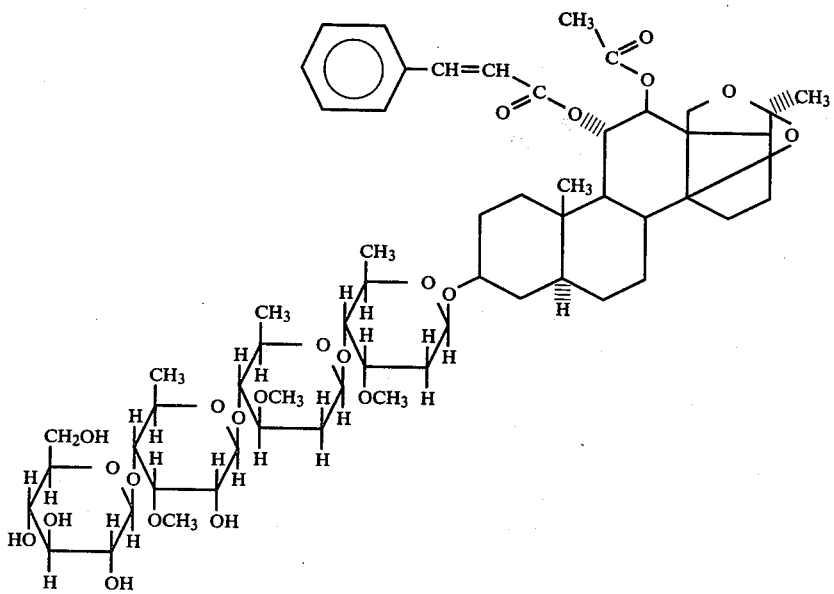

from *Marsdenia cundurango* Reichenbach fil. comprising treating an extract of *Marsdenia cundurango* Reichenbach fil. with the following three types of solvents in an optional order:
(1) a $C_{1-3}$ lower alcohol for collecting the portion which is soluble therein;
(2) chloroform or dichloromethane for collecting the portion which is soluble therein; and
(3) pentane, hexane, heptane, carbon tetrachloride, toluene or benzene for removing the portion which is soluble therein, and carrying out the following five steps successively:
(1) subjecting the extract to normal phase HPLC filler: totally porous silica gel, spherical, surface area=320 $m^2/g$; column: i.d.×1.=57 mm×300 mm; eluant: n-hexane/chloroform/methanol mixture (volumetric ratio=6:3:1); flow rate: 150 ml/min.; and detection: at RI ($1/20 \times 10^{-4}$ RIUFS) to collect a fraction chosen on the basis of the peak corresponding to Fr-2 fraction shown in FIG. 2;
(2) subjecting the extract to normal phase HPLC under the same conditions as in (1) above except that the eluant used is an n-hexane/chloroform/methanol mixture having a volumetric ratio of 6:1:1 to collect a fraction chosen on the basis of the peak corresponding to Fr-2-1 fraction shown in FIG. 3;
(3) subjecting the extract to reversed phase HPLC filler: chemically bonded silica gel-$C_8$ type, 5 μm; column: i.d.×1.=8 mm×250 mm; eluant: acetonitrile/water/diethylamine mixture (volumetric ratio=48:51.975:0.025); flow rate: 1.8 ml/min.; pressure: 150 $kg/cm^2$ and detection: at RI ($64 \times 10^{-6}$ RIUFS) to collect a fraction chosen on the basis of the peak corresponding to Fr-4 fraction shown in FIG. 8;
(4) subjecting the extract to reversed phase HPLC under the same conditions as in (3) above to collect a fraction chosen on the basis of the peak corresponding to Fr-4-1 fraction shown in FIG. 9; and
(5) subjecting the extract to normal phase HPLC filler: silica gel (totally porous crushed type, 5 μm); column: i.d.×1.=8 mm×250 mm; eluant: n-hexane/chloroform/methanol mixture (volumetric ratio=7:2:1); flow rate: 5 ml/min.; pressure: 40 $kg/cm^2$; and detection: at UV 280 nm (1.28 AUFS) to collect a fraction chosen on the basis of the one peak shown in FIG. 10.

3. A process for preparing 20-O-methyl-condurango glycoside $D_o$ represented by the formula:

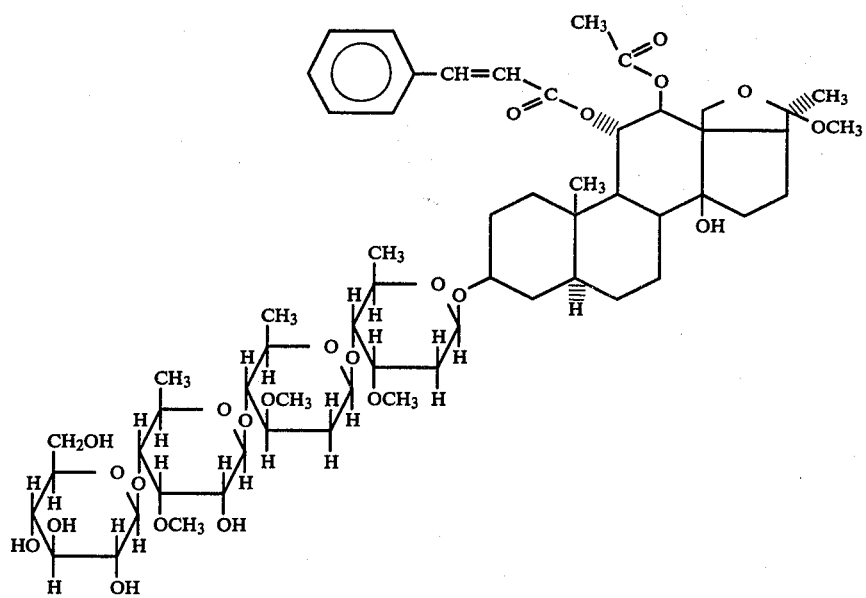

from *Marsdenia condurango* Reichenbach fil. comprising treating an extract of *Marsdenia cundurango* Reichenbach fil. with the following three types of solvents in an optional order:
(1) a $C_{1-3}$ lower alcohol for collecting the portion which is soluble therein;
(2) chloroform or dichloromethane for collecting the portion which is soluble therein; and
(3) pentane, hexane, heptane, carbon tetrachloride, toluene or benzene for removing the portion which is soluble therein, and carrying out the following five steps successively:
(1) subjecting the extract to normal phase HPLC filler: totally porous silica gel, spherical, surface area=320 m²/g; column: i.d.×l.=57 mm×300 mm; eluant: n-hexane/chloroform/methanol mixture (volumetric ratio=6:3:1); flow rate: 150 ml/min.; and detection: at RI ($1/20 \times 10^{-4}$ RIUFS) to collect a fraction chosen on the basis of the peak corresponding to Fr-2 fraction shown in FIG. 2;
(2) subjecting the extract to normal phase HPLC under the same conditions as in (1) above except that the eluant used is n-hexane/chloroform/methanol mixture having a volumetric ratio of 6:1:1 to collect a fraction chosen on the basis of the peak corresponding to Fr-2-1 fraction shown in FIG. 3;
(3) subjecting the extract to reversed phase HPLC filler: chemically bonded silica gel-$C_8$ type, 5 μm; column: i.d.×l.=8 mm×250 mm; eluant: acetonitrile/water/diethylamine mixture (volumetric ratio=48:51.975:0.025); flow rate: 1.8 ml/min.; pressure: 150 kg/cm²; and detection: at RI ($64 \times 10^{-6}$ RIUFS) to collect a fraction chosen on the basis of the peak corresponding to Fr-5 fraction shown in FIG. 8;
(4) subjecting the extract to reversed phase HPLC under the same conditions as in (3) above to collect a fraction chosen on the basis of the peak corresponding to Fr-5-1 fraction shown in FIG. 11; and
(5) subjecting the extract to normal phase HPLC filler: silica gel totally porous crushed type, 5 μm; column: i.d.×l.=8 mm×250 mm; eluant n-hexane/chloroform/methanol mixture (volumetric ratio=7:2:1); flow rate: 5 ml/min.; pressure: 40 kg/cm² and detection: at UV 280 nm (1.28 AUFS) to collect a fraction chosen on the basis of the one peak shown in FIG. 12.

4. A process for preparing condurango glycoside $A_o$ represented by the formula:

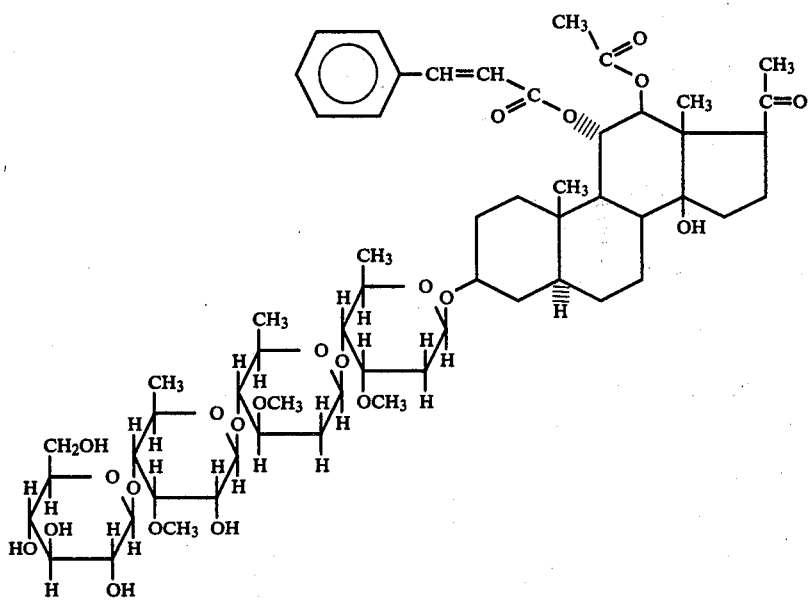

from *Marsdenia cundurango* Reichenbach fil. comprising treating an extract of *Marsdenia cundurango* Reichenbach fil. with the following three types of solvents in an optional order:
(1) a $C_{1-3}$ lower alcohol for collecting the portion which is soluble therein;
(2) chloroform or dichloromethane for collecting the portion which is soluble therein; and
(3) pentane, hexane, heptane, carbon tetrachloride, toluene or benzene for removing the portion which is soluble therein, and carrying out the following four steps successively:
(1) subjecting the extract to normal phase HPLC filler: totally porous silica gel, spherical, surface area=320 m²/g; column: i.d.×l.=57 mm×300 mm; eluant: n-hexane/chloroform/methanol mixture (volumetric ratio=6:3:1); flow rate: 150 ml/min.; and detection: at RI ($1/20 \times 10^{-4}$ RIUFS) to collect a fraction chosen on the basis of the peak corresponding to Fr-2 fraction shown in FIG. 2;
(2) subjecting the extract to normal phase HPLC under the same conditions as in (1) above except that the eluant used is n-hexane/chloroform/methanol mixture having a volumetric ratio of 6:1:1 to collect a fraction chosen on the basis of the peak corresponding to Fr-2-2 fraction shown in FIG. 3;
(3) subjecting the extract to normal phase HPLC filler: silica gel totally porous crushed type, 5 μm; column: i.d.×l.=8 mm×250 mm; eluant: n-hexane/chloroform/methanol mixture (volumetric ratio=7:2:1); flow rate: 6 ml/min.; pressure: 50 kg/cm²; and detection: at UV 250 nm (0.64 AUFS) to collect a fraction chosen on the basis of the peak corresponding to Fr-2-2-1 fraction shown in FIG. 13; and
(4) subjecting the extract to reversed phase HPLC filler: chemically bonded silica gel-$C_8$ type, 5 μm; column: i.d.×l.=8 mm×250 mm; eluant: 75% (v/v) aqueous methanol solution; flow rate: 4 ml/min.; pressure: 160 kg/cm²; and detection: at UV 280 nm (1.28 AUFS) to collect a fraction chosen on the basis of the one peak shown in FIG. 14.

Figure 15:
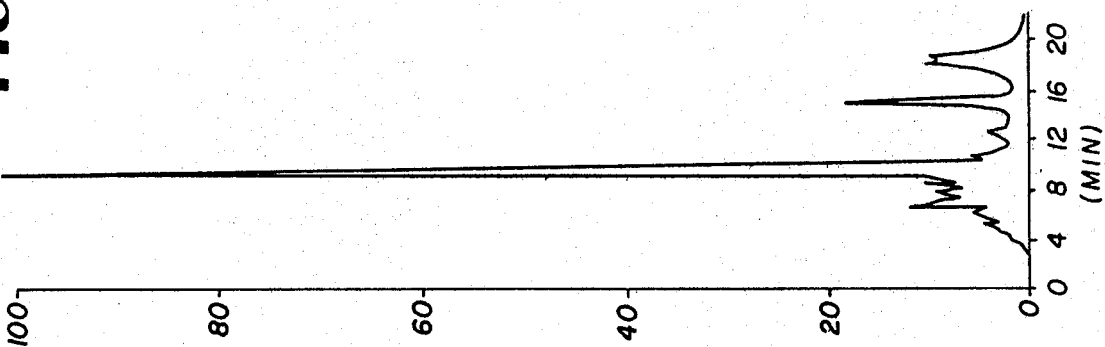
FIG. 15 shows a chart obtained when Extract B-3 was subjected to reversed phase HPLC.

5. A process for preparing condurango glycoside $C_o$ represented by the formula:

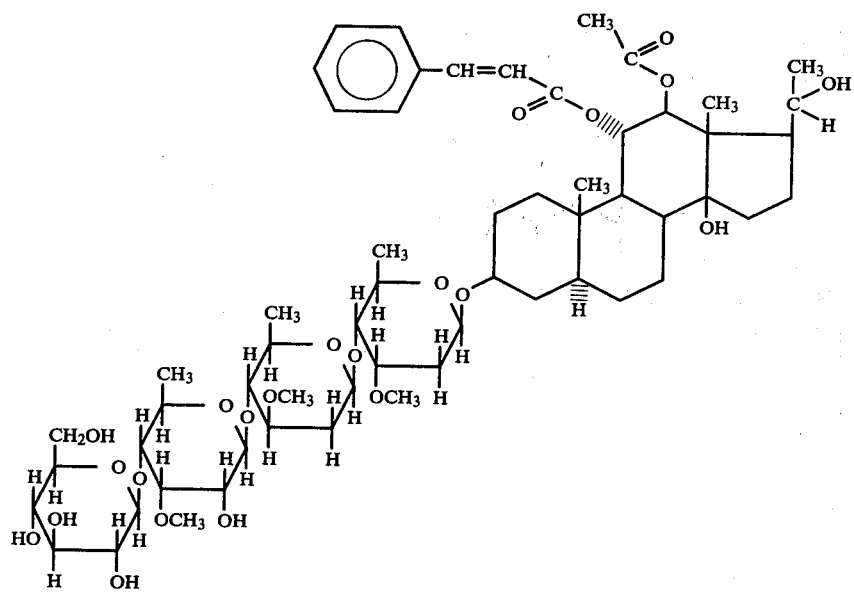

from *Marsdenia cundurango* Reichenbach fil. comprising treating an extract of *Marsdenia cundurango* Reichenbach fil. with the following three types of solvents in an optional order:

(1) a $C_{1-3}$ lower alcohol for collecting the portion which is soluble therein;

(2) chloroform or dichloromethane for collecting the portion which is soluble therein; and (3) pentane, hexane, heptane, carbon tetrachloride, toluene or benzene for removing the portion which is soluble therein, and carrying out the following three steps successively:

(1) subjecting the extract to normal phase HPLC filler: totally porous silica gel, spherical, surface area=320 m²/g; column: i.d.×l.=57 mm×300 mm; eluant: n-hexane/chloroform/methanol mixture (volumetric ratio=6:3:1); flow rate: 150 ml/min.; and detection: at RI (1/20×10⁻⁴ RIUFS) to collect a fraction chosen on the basis of the peak corresponding to Fr-3 fraction shown in FIG. 2;

(2) subjecting the extract to reversed phase HPLC filler: chemically bonded silica gel-$C_{18}$ type; column: i.d.×l.=57 mm×300 mm; eluant: 70% (v/v) aqueous methanol solution; flow rate: 100 ml/min.; and detection: at RI (1/50×10⁻⁴ RIUFS) to collect a fraction chosen on the basis of the peak corresponding to Fr-3-1 fraction shown in FIG. 6;

(3) subjecting the extract to reversed phase HPLC filler: chemically bonded silica gel-$C_8$ type, 5 μm; column: i.d.×l.=8 mm×250 mm; eluant: 50% (v/v) aqueous acetonitrile solution; flow rate: 4 ml/min.; pressure: 150 kg/cm²; and detection: at UV 250 nm (0.64 AUFS) to collect a fraction chosen on the basis of the one peak shown in FIG. 15.

6. A process for preparing 20-iso-O-methyl-condurango glycoside $D_o$ represented by the formula:

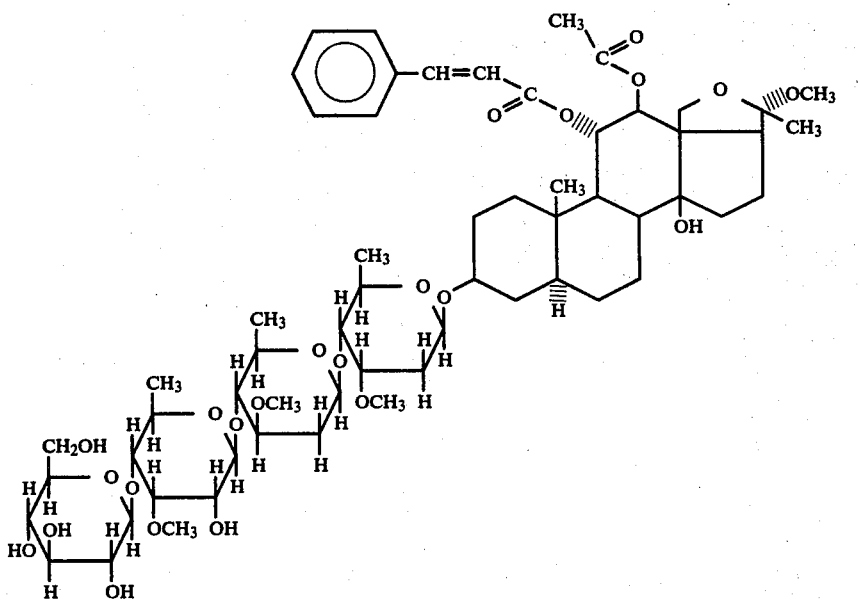
which comprises subjecting condurango glycoside $B_o$ represented by the formula:
to alcoholysis with a $10^{-6}$–$10^{-4}$ molar concentration of acetic acid solution in methanol or a 0.001 N–0.01 N oxalic acid solution in methanol.
7. A process for preparing condurango glycoside $D_o$ represented by the formula:
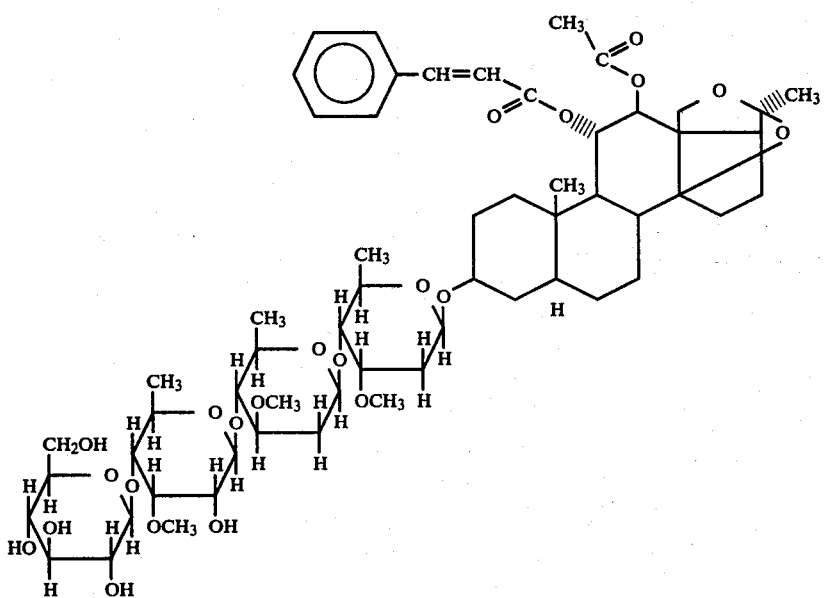

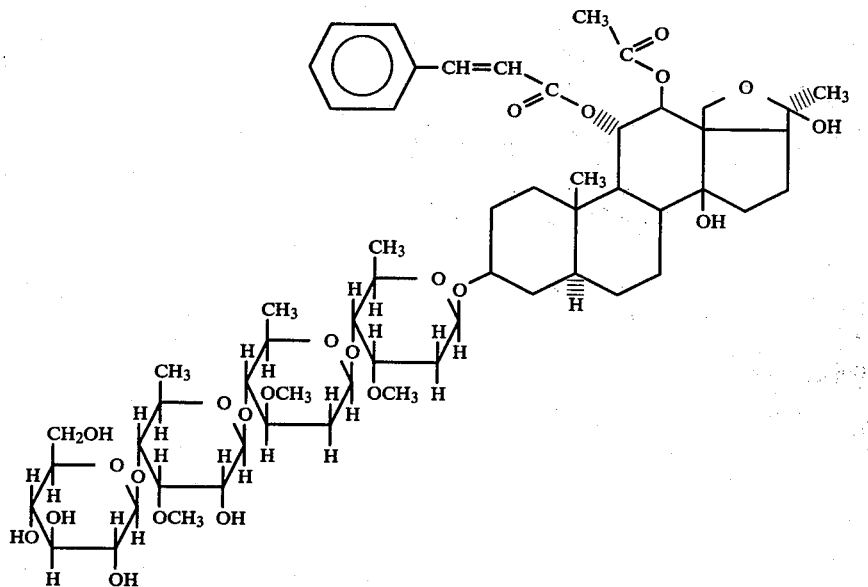
which comprises subjecting condurango glycoside $B_o$ represented by the formula:
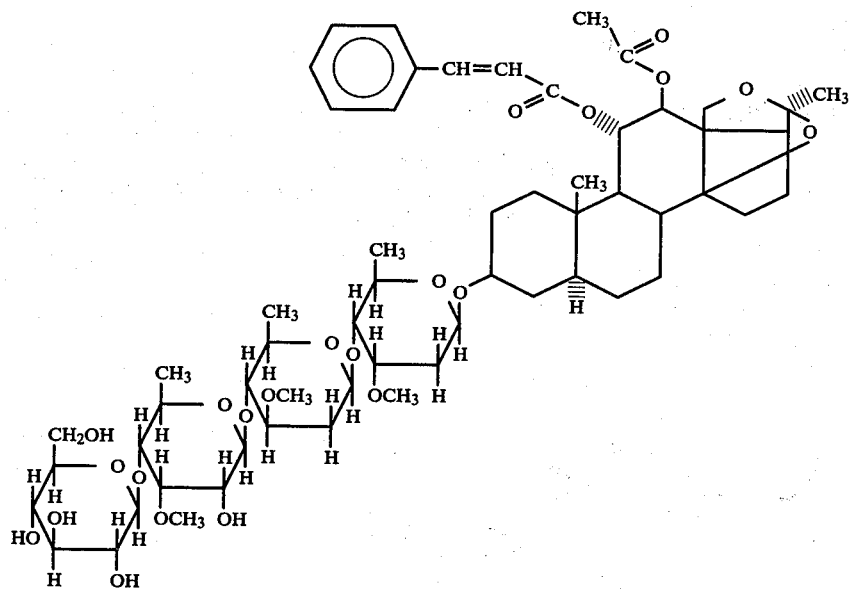
to hydrolysis with water.
8. A pharmaceutical composition effective against Ehrlich carcinoma tumor comprising a compound as described in claim 1 in an amount effective against Ehrlich carcinoma in admixture with a pharmaceutically acceptable diluent or carrier.
* * * * *